(12) United States Patent
Orion et al.

(10) Patent No.: US 9,265,632 B2
(45) Date of Patent: Feb. 23, 2016

(54) METHODS OF SUPPORTING A VEIN

(71) Applicants: Vascular Graft Solutions Ltd., Tel-Aviv (IL); The Medical Research, Infrastructure and Health Services Fund of the Tel Aviv Medical Center, Tel-Aviv (IL)

(72) Inventors: Eyal Orion, Ramat-Efal (IL); Yehuda Bachar, Givat Shmuel (IL); Yanai Ben-Gal, Ramat-HaSharon (IL); Avraham Rapaport, Tel-Aviv (IL); Gilad Cibulski, Zur-Moshe (IL); Ronny Winshtein, Ramat-HaSharon (IL)

(73) Assignees: VASCULAR GRAFT SOLUTIONS LTD., Tel-Aviv (IL); THE MEDICAL RESEARCH, INFRASTRUCTURE AND HEALTH SERVICES FUND OF THE TEL AVIV MEDICAL CENTER, Tel-Aviv (IL)

( * ) Notice: Subject to any disclaimer, the term of this patent is extended or adjusted under 35 U.S.C. 154(b) by 0 days.

(21) Appl. No.: 14/287,030

(22) Filed: May 25, 2014

(65) Prior Publication Data

US 2014/0257462 A1    Sep. 11, 2014

Related U.S. Application Data

(63) Continuation of application No. 13/130,760, filed as application No. PCT/IL2009/001105 on Nov. 24, 2009, now Pat. No. 8,734,503.

(60) Provisional application No. 61/244,138, filed on Sep. 21, 2009, provisional application No. 61/186,046, filed on Jun. 11, 2009, provisional application No. 61/193,398, filed on Nov. 24, 2008.

(51) Int. Cl.
*A61F 2/82* (2013.01)
*A61F 2/06* (2013.01)
(Continued)

(52) U.S. Cl.
CPC . *A61F 2/82* (2013.01); *A61F 2/064* (2013.01); *A61B 17/11* (2013.01); *A61B 17/12* (2013.01); *A61B 2017/1107* (2013.01); *A61B 2017/1135* (2013.01); *A61F 2/90* (2013.01)

(58) Field of Classification Search
CPC .......... A61F 24/18; A61F 2/22; A61F 2/2412; A61F 2/82
USPC ................................................. 623/1.15–1.48
See application file for complete search history.

(56) References Cited

U.S. PATENT DOCUMENTS 3,626,947 A    12/1971  Sparks
4,158,984 A    6/1979   Griffiths
(Continued)

FOREIGN PATENT DOCUMENTS

JP    08-509406      7/1997
JP    2006-507092    3/2006
(Continued)

OTHER PUBLICATIONS

Notice of Reason for Rejection Dated Jun. 20, 2014 From the Japanese Patent Office Re. Application No. 2011-537010 and Its Translation Into English.

(Continued)

*Primary Examiner* — Suzette J Gherbi
(74) *Attorney, Agent, or Firm* — Clements Bernard PLLC; Christopher L. Bernard; Lawrence A. Baratta, Jr.

(57) ABSTRACT

Methods of supporting a vein, featuring deforming a vein support while being mounted on the vein. Such deformation may be sufficient to impose thereupon a plastic deformation that alters a length of the vein support, from a pre-deformation relaxed length to a post-deformation relaxed length different than the pre-deformation relaxed length. Following the plastic deformation, the vein support may maintain a new shape relative to a longitudinal axis thereof.

42 Claims, 18 Drawing Sheets

(51) Int. Cl.
*A61B 17/11* (2006.01)
*A61B 17/12* (2006.01)
*A61F 2/90* (2013.01)

(56) References Cited

U.S. PATENT DOCUMENTS

| | | | |
|---|---|---|---|
| 4,173,689 | A | 11/1979 | Lyman et al. |
| 4,466,139 | A | 8/1984 | Ketharanathan |
| 4,743,251 | A | 5/1988 | Barra |
| 5,084,065 | A | 1/1992 | Weldon et al. |
| 5,468,242 | A * | 11/1995 | Reisberg ............ 606/285 |
| 5,476,471 | A * | 12/1995 | Shifrin et al. ......... 606/151 |
| 5,556,414 | A * | 9/1996 | Turi ................ 623/1.11 |
| 5,584,876 | A | 12/1996 | Bruchman et al. |
| 5,645,581 | A | 7/1997 | Zurbruegg |
| 5,681,278 | A | 10/1997 | Igo et al. |
| 5,755,659 | A | 5/1998 | Zurbrügg |
| 5,824,047 | A | 10/1998 | Moreland |
| 5,876,356 | A | 3/1999 | Viera et al. |
| 6,015,422 | A | 1/2000 | Kerr |
| 6,071,306 | A | 6/2000 | Angelini |
| 6,102,918 | A | 8/2000 | Kerr |
| 6,136,022 | A | 10/2000 | Nunez et al. |
| 6,168,620 | B1 | 1/2001 | Kerr |
| 6,187,038 | B1 | 2/2001 | Sullivan et al. |
| 6,250,193 | B1 | 6/2001 | Head |
| 6,358,275 | B1 | 3/2002 | McIlroy et al. |
| 7,060,022 | B2 | 6/2006 | Chen et al. |
| 7,069,835 | B2 | 7/2006 | Nishri et al. |
| 7,083,644 | B1 | 8/2006 | Moroni |
| 7,093,527 | B2 | 8/2006 | Rapaport et al. |
| 7,211,109 | B2 | 5/2007 | Thompson |
| 7,223,286 | B2 | 5/2007 | Wright et al. |
| 7,275,471 | B2 | 10/2007 | Nishri et al. |
| 7,318,835 | B2 | 1/2008 | Berra |
| 7,329,276 | B2 | 2/2008 | Smith et al. |
| 7,455,739 | B2 | 11/2008 | Zhou |
| 7,666,222 | B2 | 2/2010 | Wright et al. |
| 7,998,188 | B2 | 8/2011 | Zilla et al. |
| 8,057,537 | B2 | 11/2011 | Zilla et al. |
| 8,172,746 | B2 | 5/2012 | Zilla et al. |
| 8,382,814 | B2 | 2/2013 | Zilla et al. |
| 8,388,616 | B2 | 3/2013 | Vogel et al. |
| 2003/0191518 | A1 | 10/2003 | Spiridigliozzi et al. |
| 2004/0102837 | A1 | 5/2004 | Boyle et al. |
| 2004/0158316 | A1 | 8/2004 | Jonkman et al. |
| 2004/0162606 | A1* | 8/2004 | Thompson ............ 623/1.22 |
| 2004/0167605 | A1 | 8/2004 | Elliott |
| 2004/0215309 | A1 | 10/2004 | Moritz et al. |
| 2005/0055082 | A1* | 3/2005 | Ben Muvhar et al. ...... 623/1.15 |
| 2005/0131520 | A1 | 6/2005 | Zilla et al. |
| 2005/0261780 | A1* | 11/2005 | Heino et al. ............ 623/23.51 |
| 2006/0149348 | A1 | 7/2006 | Vogel et al. |
| 2007/0207186 | A1 | 9/2007 | Scanlon et al. |
| 2007/0293932 | A1 | 12/2007 | Zilla et al. |
| 2008/0114391 | A1* | 5/2008 | Dieck et al. ............ 606/200 |
| 2008/0208323 | A1 | 8/2008 | El-Kurdi et al. |
| 2008/0300451 | A1 | 12/2008 | Beck et al. |
| 2009/0005857 | A1* | 1/2009 | Ischinger ............ 623/1.18 |
| 2009/0138065 | A1 | 5/2009 | Zhang et al. |
| 2009/0306764 | A1 | 12/2009 | Zilla et al. |
| 2011/0077729 | A1 | 3/2011 | Gross et al. |
| 2011/0295157 | A1 | 12/2011 | Zilla et al. |
| 2012/0116495 | A1 | 5/2012 | Zilla et al. |
| 2013/0085564 | A1 | 4/2013 | Papp et al. |
| 2013/0123902 | A1 | 5/2013 | Iancea et al. |
| 2013/0144374 | A1 | 6/2013 | Zilla et al. |

FOREIGN PATENT DOCUMENTS

| | | |
|---|---|---|
| WO | WO 95/03010 | 2/1995 |
| WO | WO 97/33532 | 9/1997 |
| WO | WO 99/56667 | 11/1999 |
| WO | WO 00/53121 | 9/2000 |
| WO | WO 01/26707 | 4/2001 |
| WO | WO 02/098325 | 12/2002 |
| WO | WO 03/011190 | 2/2003 |
| WO | WO 2004/026178 | 4/2004 |
| WO | WO 2004/047613 | 6/2004 |
| WO | WO 2004/096095 | 11/2004 |
| WO | WO 2005/044142 | 5/2005 |
| WO | WO 2006/018268 | 2/2006 |
| WO | WO 2006/054968 | 5/2006 |
| WO | WO 2006/072934 | 7/2006 |
| WO | WO 2006/082574 | 8/2006 |
| WO | WO 2007/140564 | 12/2007 |
| WO | WO 2008/070996 | 6/2008 |
| WO | WO 2008/120184 | 10/2008 |
| WO | WO 2008/125842 | 10/2008 |
| WO | WO 2008/150878 | 12/2008 |
| WO | WO 2009/043026 | 4/2009 |
| WO | WO 2010/058406 | 5/2010 |

OTHER PUBLICATIONS

Office Action Dated May 16, 2014 From the State Intellectual Property Office of the People's Republic of China Re. Application No. 200980155497.1 and Its Translation into English.
Search Report Dated May 16, 2014 From the State intellectual Property Office of the People's Republic of China Re. Application No. 200980155497.1 and Its Translation Into English.
Communication Pursuant to Article 94(3) EPC Dated May 2, 2013 From the European Patent Office Re. Application No. 09796098.3.
Communication Pursuant to Rules 161(1) and 162 EPC Dated Jul. 6, 2011 From the European Patent Office Re. Application No. 09796098.3.
International Preliminary Report on Patentability Dated Feb. 2, 2011 From the International Preliminary Examining Authority Re. Application No. PCT/IL2009/001105.
International Search Report and the Written Opinion Dated Mar. 9, 2010 From the International Searching Authority Re. Application No. PCT/IL2009/001105.
Notice of Reason for Rejection Dated Nov. 8, 2013 From the Japanese Patent Office Re. Application No. 2011-537010 and Its Translation Into English.
Office Action Dated Apr. 25, 2013 From the Israel Patent Office Re. Application No. 213111 and Its Translation Into English.
Official Action Dated Aug. 14, 2013 From the US Patent and Trademark Office Re. U.S. Appl. No. 13/130,760.
Translation of Office Action Dated Aug. 1, 2013 From the State Intellectual Property Office of the People's Republic of China Re. Application No. 200980155497.1.
Translation of Search Report Dated Aug. 1, 2013 From the State Intellectual Property Office of the People's Republic of China Re. Application No. 200980155497.1.

* cited by examiner

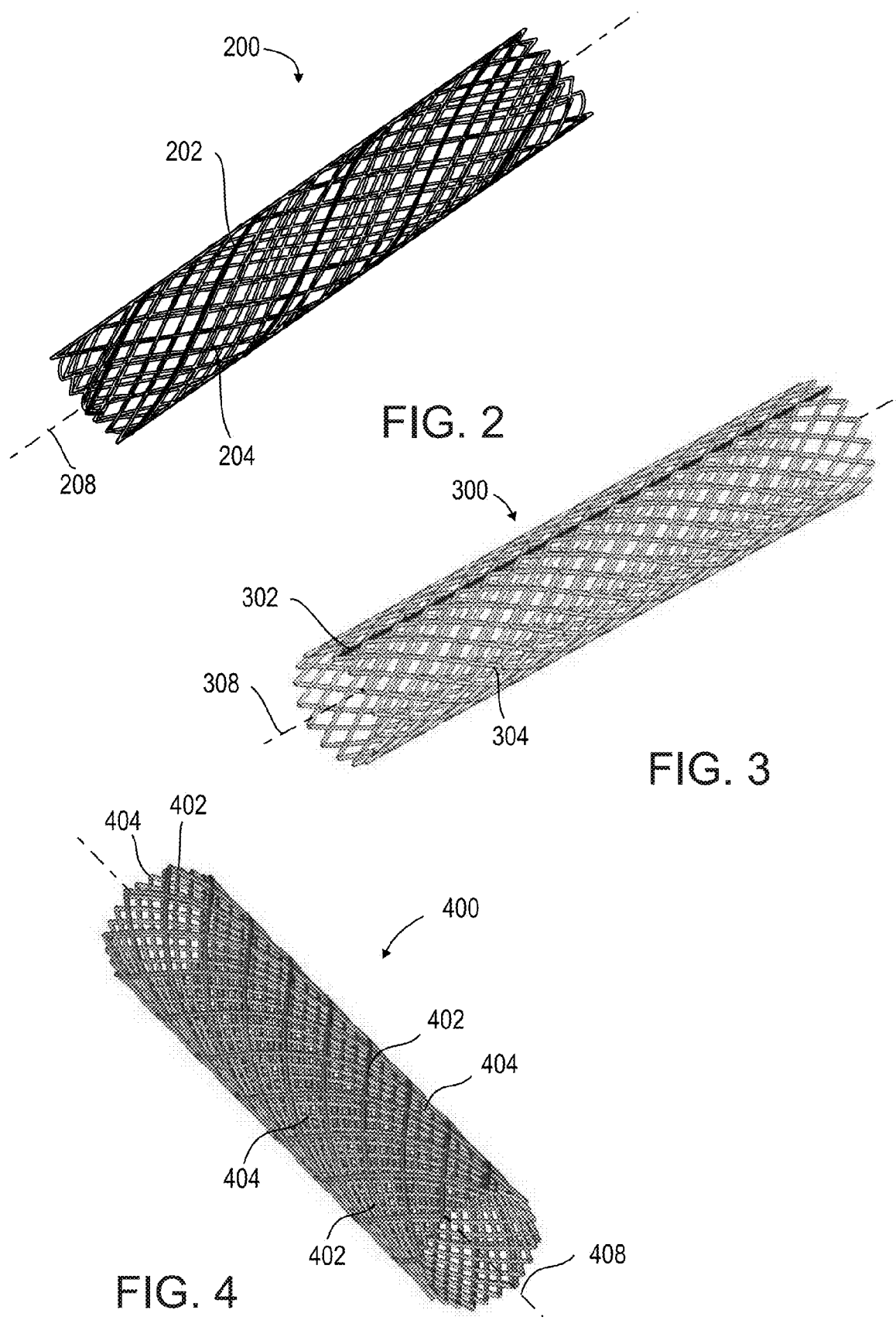

METHODS OF SUPPORTING A VEIN

RELATED APPLICATIONS

This application is a continuation of U.S. patent application Ser. No. 13/130,760 filed on May 24, 2011 which is a National Phase of PCT Patent Application No. PCT/IL2009/001105 having International filing date of Nov. 24, 2009, which claims the benefit of priority of U.S. Provisional Patent Application Nos. 61/244,138 filed on Sep. 21, 2009, 61/186,046 filed on Jun. 11, 2009 and 61/193,398 filed on Nov. 24, 2008. The contents of all of the above documents are incorporated by reference as if fully set forth herein.

FIELD AND BACKGROUND OF THE INVENTION

The present invention, in some embodiments thereof, relates to a support for a conduit in a body of a person or an animal, and in particular to a support for a grafted vessel inside a body.

Coronary Heart Disease (CHD) is considered one of the leading causes of death in both men and women. The disease pathophysiology involves a buildup of cholesterol plaque in a blood vessel to a point where the vessel may be partially, or wholly, occluded.

Two known techniques for treating occluded coronary vessels are Percutaneous Transluminal Coronary Angioplasty (PTCA) for opening the stenotic area with a balloon catheter, usually accompanied by placement of a stent to secure the opening; and Coronary Artery Bypass Graft (CABG) surgery for bypassing an occluded vessel with a graft implant. Several types of (autologous) coronary artery bypass grafts are known, such as internal thoracic grafts, radial and right gastroepiploic artery grafts, and saphenous vein grafts. These grafts generally originate from the aorta or its bifurcations or are constructed grafts. Synthetic grafts are generally considered alternative to autologous grafts, although their overall performance and patency is still investigated.

Blood flow through a grafted vessel may depend on multiple factors such as vessel length, diameter, shape, angles, flow patterns, etc. The graft position in relation to a target vessel (the vessel to which the graft connects at a distal end) has also an important impact on the flow. For normal blood flow through the bypass to the target vessel, the graft is generally required to be substantially patent, without stenosis or flow disturbances, such as turbulent flow.

U.S. Pat. No. 4,743,251 "VEIN PROTHESIS AND METHOD FOR PRODUCING SAME", relates to a prothesis "intended to be implanted in a human patient for forming an aorto-coronary by-pass or another by-pass on other arteries. The prosthesis comprises a normal, unaltered living vein which is taken from the patient himself/herself and which is surrounded by a multiperforated flexible sheath. The inside diameter of the sheath is so chosen that, after implantation, the outside diameter of the vein is maintained by the sheath at a value less than the maximum possible diameter of the vein and that the inside diameter of the vein is suitable for the diameter of the receiver artery."

U.S. Pat. No. 5,755,659 "METHOD OF MAKING A VASCULAR PROSTHESIS", relates to "a vascular prosthesis for the replacement of blood vessels in the human or animal body, consisting of a section of a replacement blood vessel (3) which has been taken from a human or animal body and a fibro-elastic tube (2) which is drawn over this vascular section, whose intersecting threads (1) which form the tube wind in spiral form around the longitudinal axis of the tube, wherein the fibro-elastic tube (2) is extended pointwise in the longitudinal direction with alteration of the diameter or is compressed and thereby is caused to contact the replacement vessel evenly over its total area."

US Patent Publication No. 2004/0215309 "COVERING ELEMENT FOR VEINS, METHOD FOR THE PRODUCTION AND USE THEREOF IN SURGERY", relates to "sheathing for reinforcing natural veins for use as surgical implants in the form of textile netting that is configured by forming a seamless, tubular, essentially pile-less, knit fabric and has loops having large, open apertures having essentially polygonal shapes is made available."

US patent Publication 2007/0293932 "COMPLIANT BLOOD VESSEL GRAFT", relates to "stents and methods of using stents are provided. Stents of the invention provide external support structure for a blood vessel segment disposed within, wherein the stents are capable of resilient radial expansion in a manner mimicking the compliance properties of an artery. The stent may be formed of a knitted or braided mesh formed so as to provide the needed compliance properties. A venous graft with the stent and a vein segment disposed within is provided, wherein graft is capable of mimicking the compliance properties of an artery. Methods of selecting stents for downsizing and methods of using the stents of the invention in downsizing and smoothening are provided. Methods of replacing a section of an artery with a venous graft including a stent of the invention are provided. Methods of reducing intimal hyperplasia in implanted vein segment in a venous graft using stents of the invention are provided."

U.S. Pat. No. 6,071,306, "EXTERNALLY STENTED VEIN SEGMENT AND ITS USE IN AN ARTERIO-VENOUS BYPASS GRAFTING PROCEDURE", relates to "an arteriovenous bypass grafting procedure in which a vein segment is implanted into the arterial circulation of a mammalian subject, wherein a non-restrictive porous stent is provided around the grafted vein."

SUMMARY OF THE INVENTION

According to an aspect of some embodiments of the present invention there is provided an external vein support comprising an elongate axial body including an axis, the body comprising axial plasticity so that it is plastically deformable by at least one of stretching, bending, twisting, and any combination thereof, relative to the axis. Optionally, the body is fixedly deformable in diameter at a plurality of points along a length of the body. Optionally, the body is radially elastic in at least one point of the plurality of points fixedly deformed.

According to some embodiments of the present invention, the body comprises a substantially non-uniform diameter. Optionally, the body comprises a plurality of fibers arranged so that at a first average diameter, the springback of said body relative to the axis is substantially greater than at a second average diameter. Optionally, a reduction of the diameter decreases a percentage of the springback. Optionally, the percentage of the springback ranges from 0.5% to 50%.

According to some embodiments of the present invention, the axis is a longitudinal axis of the axial body. Optionally, the axis is a transverse axis of the axial body. Additionally or alternatively, a reduction of the diameter decreases the resilience. Optionally, a reduction of the diameter increases the resilience.

According to some embodiments of the present invention, the body comprises a plurality of fibers arranged so that the support is radially elastic having previously been fixedly deformed. Optionally, the body comprises at least one plastically deformable element. Optionally, the plastically deformable element is a plastically deformable fiber. Additionally or alternatively, the at least one plastically deformable fiber is spirally interlaced along the body.

According to some embodiments of the present invention, the body comprises a plurality of non-plastically deformable elements. Optionally, at least one of the non-plastically deformable elements is an elastic fiber.

According to some embodiments of the present invention, the support further comprises an extension attachable to an end portion of the body. Optionally, the extension comprises a first opening and a second opening, the second opening skewed relative to the first opening and forming an angle ø between 20 and 80 degrees relative to said axis. Additionally or alternatively, an end portion of the body is elastically deformable longitudinally along the axis.

According to an aspect of some embodiments of the present invention there is provided a method of mounting a vein, comprising attaching a vein to at least two separate points in a vascular system; allowing blood to flow in and expand the vein; and shaping a vein support element mounted on the vein during the flowing. Optionally, shaping the vein support comprises plastically deforming the body by stretching the support along an axis. Optionally, shaping the vein support comprises plastically deforming the body by compressing the support along the axis. Optionally, shaping the vein support comprises plastically deforming the body by axially bending the support.

According to some embodiments of the present invention, the method comprises including a radially elastic portion along a length of the body. Optionally, the method comprises decreasing springback by reducing the diameter.

According to an aspect of some embodiments of the present invention there is provided an extendable stent having at least two plastically deformable elements intersecting to form a braiding angle, wherein a plasticity of the stent in one or more axes increases as the angle decreases from a larger angle in a stent first less extended position, to a smaller angle in a stent second more extended position. Optionally, the braiding angle is between 30 degrees and 150 degrees, inclusively. Optionally, the axes are one or more of: longitudinal axis, radial axis and transverse axis. Alternatively or additionally, a plasticity of the stent in one or more axes decreases as the angle decreases from a larger angle in a stent first less extended position, to a smaller angle in a stent second more extended position. In an exemplary embodiment, when the stent angle decreases, the stent achieves increased plasticity in its longitudinal and/or transverse axes while lowering its radial plasticity (e.g., becomes more radially elastic).

According to an aspect of some embodiments of the present invention there is provided a method of increasing a plasticity of an extendable stent having at least two plastically deformable elements intersecting to form a braiding angle, by decreasing the braiding angle by extending said stent from a first less extended position to a second more extended position.

According to an aspect of some embodiments of the present invention there is provided a vein support for mounting on along vein, comprising a body adapted to cover at least partially the vein and elastically resist changes in diameter thereof along the vein, the body including at least one elongate plastically deformable structure which extends along the vein.

According to an aspect of some embodiments of the present invention there is provided a tubular implant including a plurality of fibers arranged so that at a first diameter, the elastic deformation of the support causes springback and at a second diameter, the plastic deformation reduces springback.

According to an aspect of some embodiments of the present invention there is provided a method of matching a vein support element to a vein diameter, comprising: providing an elongate vein support element; and fixedly deforming the vein support to have at least 2 different diameters therealong. Optionally, the method comprises resiliently resisting changes in diameter of the support, by the support.

According to an aspect of some embodiments of the present invention there is provided a method of supporting a vein, comprising mounting a support on a vein; and thereafter matching a length of said support, by non-elastic deforming thereof to at least cover a plurality of anastomosis region on the vein.

According to an aspect of some embodiments of the present invention there is provided a method of supporting a vein, comprising mounting a support on a vein; and thereafter non-elastically deforming the support to define a layout of the vein independent of any attachment of the support to tissue other than the vein.

According to an aspect of some embodiments of the present invention there is provided a method of supporting a vein, comprising mounting a support on a vein; and thereafter deforming the support diameter to match the vein. Optionally, deforming comprises providing different diameters along the support.

According to an aspect of some embodiments of the present invention there is provided a vein support for mounting on along vein, comprising a body adapted to cover at least partially the vein and elastically resist changes in diameter thereof along the vein, the body including at least one elongate plastically deformable structure which extends along the vein.

According to an aspect of some embodiments of the present invention there is provided a method of adapting a vein support to a vein, comprising mounting at least a part of a vein support on a vein; adjusting a diameter of the portion; and repeating the adjustment for consecutive axial portions of the vein support. Optionally, adjusting comprises modifying a diameter by changing an axial length of the portion.

According to an aspect of some embodiments of the present invention there is provided a method and device for providing a desired blood flow between a first point in a vascular system of a patient and a second point in the vascular system. A "desired blood flow" may be achieved by avoiding graft radial and/or axial and/or transverse deformation, or any other type of deformation or any combination thereof. Such deformations may be caused by vein graft inflation under arterial pressures, diameter mismatches between a vein graft and host artery, and/or intimal/medial hyperplasia. The method comprising positioning a vein within a lumen of a vein support, attaching a first end of the vein to the first point in the vascular system with a first anastomosis so as to incorporate the vein into the vascular system, and deforming the vein support in response to the vascular system so that a lumen of the vein is selectively reshaped to provide the desired bloodflow. "In response to vascular system" may mean, for example, in response to measured arterial pressure after connecting the bypass, and allowing blood flow therein, the surgeon can determine more accurately the diameter, length and overall shape of the graft and derive the specific pre-deformation and/or post-deformation properties of the graft/vein support. Optionally, the vein support is deformed by manipulating the vein support sufficiently to impose a plastic deformation of the vein support that alters a length of the vein support from a pre-deformation relaxed length to a post-deformation relaxed length different than the pre-deformation relaxed length, and wherein the manipulation of the vein support is performed while the vein is disposed in the vein support. Optionally, the length of the vein support is coupled to a cross-sectional diameter of the vein support so that the plastic deformation alters the diameter from a pre-deformation relaxed diameter to a post-deformation relaxed diameter different than the pre-deformation relaxed diameter, and wherein the post-deformation diameter is selected in response to a diameter of the vein. Additionally or alternatively, the vein has the vein diameter at a first axial location of the vein and another vein diameter at a second axial location of the vein, wherein the manipulation of the vein support is performed so that the vein support has the vein support diameter adjacent the first axial location and a second vein support diameter corresponding to the second vein diameter adjacent the second axial location.

According to some embodiments of the present invention, the vein support is deformed by manipulating the vein support sufficiently to impose a plastic deformation of the vein support that alters a path of the lumen between the first point and the second point from a first relaxed axial path to a second relaxed axial path, the second path defining a different angle relative to the adjacent vascular system at the first point than the first path so that laminar flow through the vein is promoted by the manipulation of the vein support, and wherein the manipulation of the vein support is performed while the vein is disposed in the vein support.

According to some embodiments of the present invention, the vein support responds elastically to physiological stress associated with the bloodflow, and wherein the vein support responds plastically to manually imposed stress associated with the deforming of the vein support, the response of the vein support differing significantly from a compliance of natural arteries of the vascular system.

According to an aspect of some embodiments of the present invention there is provided a vein support for use with a vein to help provide a desired blood flow between a first point in a vascular system of a patient and a second point in the vascular system by incorporation of the vein into the vascular system, the vein support comprising an elongate body having a first end and a second end with a channel therebetween, the elongate body having a relaxed pre-deformation configuration, the channel sized to freely receive the vein when the body is in the pre-deformation configuration so that an axis of the channel extends along an axis of the vein; and the body being manually manipulatable from the pre-deformation configuration to a relaxed post-deformation configuration selected in response to the vascular system, the channel in the post-deformation configuration supporting receiving the vein therein so as to inhibit tissue-response induced occlusion of the desired flow.

According to some embodiments of the present invention, the axial body is manipulatable from a pre-deformation relaxed length to a post-deformation relaxed length different than the pre-deformation relaxed length. Optionally, the post-deformation relaxed length is substantially greater than the pre-deformation relaxed length. Optionally, the post-deformation relaxed length is substantially smaller than the pre-deformation relaxed length. Additionally or alternatively, the post-deformation relaxed length is substantially equal to the length of the graft. Optionally, the graft is a saphenous vein graft. Optionally, the axial body is substantially tubular when in the pre-deformation relaxed length. Optionally, the axial body is substantially conical when in the post-deformation relaxed length. Additionally or alternatively, the axial body is substantially tubular when in the post-deformation relaxed length.

According to some embodiments of the present invention, manipulating the axial body to the post-deformation relaxed length allows natural cell growths through a periphery of the axial body, thereby naturally producing a composite graft. Optionally, the composite graft is substantially rigid. Optionally, the composite graft substantially differs from a native human coronary artery in at least one mechanical property. Additionally or alternatively, the composite graft substantially mimics a native human coronary artery in at least one mechanical property. Optionally, the mechanical property is radial compliance. Optionally, the composite graft length is substantially the same as the post-deformation relaxed length.

According to some embodiments of the present invention, the external vein support is configured to form the composite graft using natural cell growth through a periphery of the axial body when in the post-deformation relaxed length. Optionally, the vein support is capable of resilient radial expansion in a manner providing compliance in the range of 3-30%/100 mm Hg. Optionally, the vein support is capable of resilient radial expansion in a manner providing compliance less than 5%/100 mm Hg.

According to some embodiments of the present invention, the axial body is further manipulatable to a chosen substantially non-linear contoured path. Optionally, the composite graft contour is substantially the same as the chosen substantially nonlinear contoured path.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 schematically illustrates an exemplary vein support, in accordance with some embodiments of the present invention;

FIG. 3 schematically illustrates an exemplary vein support, in accordance with some embodiments of the present invention;

FIG. 4 schematically illustrates an exemplary vein support, in accordance with some embodiments of the present invention;

DESCRIPTION OF EMBODIMENTS OF THE INVENTION

Figure 1A:
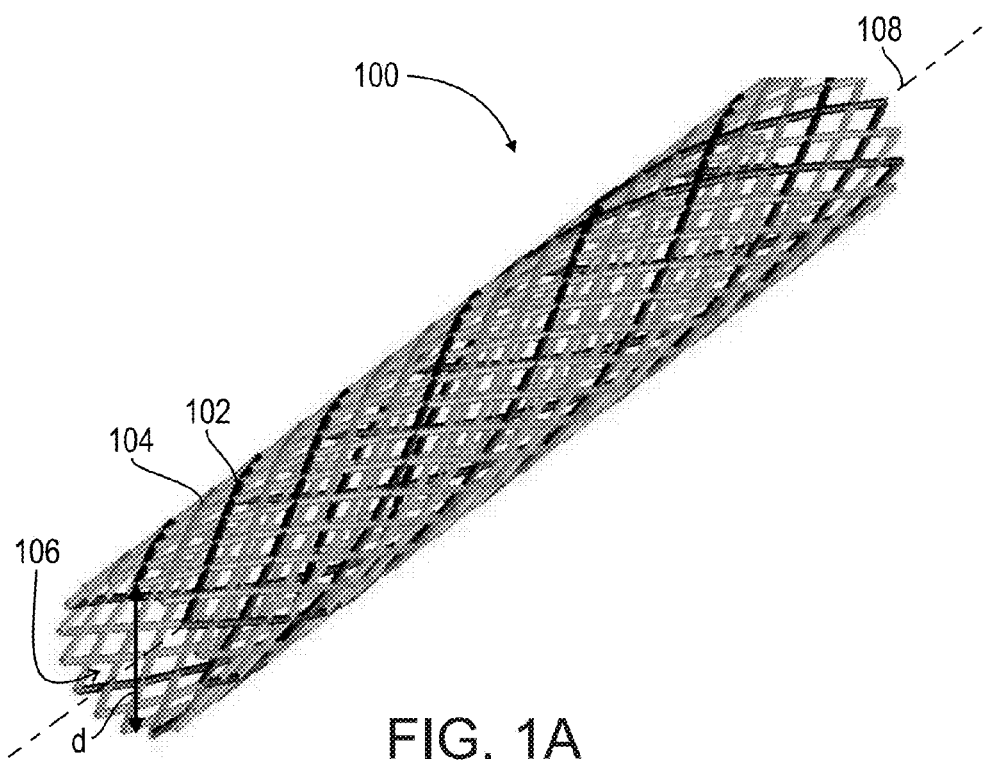
FIG. 1A schematically illustrates an isometric view of an exemplary vein support, in accordance with an embodiment of the present invention.

The present invention, in some embodiments thereof, relates to a support for a conduit in a body of a person or an animal, and in particular to a support for a grafted vessel inside a body.

An aspect of some embodiments of the present invention relates to a vein support for supporting body vessels such as, for example, blood vessels, wherein the support may be fixedly displaced relative to a longitudinal axis of the support by plastically deforming the support relative to the axis. Plastically deforming the support relative to it longitudinal axis includes plastically stretching the support along the axis and/or plastically bending the support in a direction transversally to the axis, with minimal (elastic) springback in the support (minimal elasticity such that the support substantially maintains its new shape relative to the axis from a perspective of an operator attaching the support). Optionally, the support may be plastically deformed to a plurality of points along the axis. Optionally, the support may be plastically reversely compressed in a direction along the axis.

In some embodiments of the present invention, the support, which may be tubular in shape, may include a diameter which may be fixedly deformed along a plurality of points of the longitudinal axis. This allows different portions (segments) of the support to have different diameters, optionally facilitating uniform support of a vessel with a varying cross-sectional diameter along its length, as for example in cases where the supported vessel is of non-uniform cross-section. Optionally, the support may include a radially elastic portion along a length of the support. Radial elasticity allows the segment to regain its fixedly deformed diameter despite application of a compressive force at one or more points along a circumference of the segment (once the compressive force is removed, the segment returns to the fixedly deformed diameter and does not remain deformed due to the applied force). A potential benefit of radial elasticity is that the vessel may return to its original shape once the compressive force is removed, and does not remain "pinched" by a permanent deformation of the support. In some embodiments, the radial elasticity is substantially maintained or increases as the diameter of the segment decreases and a length of the support increases. Alternatively, the radial elasticity decreases in such circumstances.

In some embodiments of the present invention, the support includes a meshed surface having at least one plastically deformable element. The mesh may be of any woven or non-woven type/design, including but not limited to: knitting, braiding, felting, crocheting, weaving and/or needling of a textile. Optionally, the support further includes at least one elastic member. In some embodiments of the present invention, the support includes a braid comprising at least one plastically deformable element. Optionally, the braid includes a plurality of deformable elements, some of which may be elastically deformable. Optionally, the plastically deformable element and/or the elastically deformable element include fibers. Optionally, the fibers are made of a biocompatible material and/or are treated and/or covered with a biocompatible material. Optionally, at least one fiber is biodegradable, and may degrade and/or be absorbed in body for example between 3 to 18 months from day of treatment. Optionally, the support or at least one of its fibers includes drug eluting capabilities. A drug may be administered in a gradual manner towards the supported vessel outer surface (i.e., adventitia) and may permeate into vessel wall and/or inner volume thereof.

In some embodiments of the present invention, an end portion in the plastically deformable elements (in an end portion of the support) is substantially blunted, for example through a heat treatment which may include laser heating (for example laser welding or soldering), so as to reduce a possibility of injury to a vessel, or optionally a body organ, due to prickling or piercing by the end portion. Optionally, the end portion in the plastically deformable element may be looped together with an end portion of a second plastically deformable element, and the end portions attached to the support (for example, by welding) so that they do not protrude outwards. Optionally, the end portions of the first element and the second element are connected together by the heat treatment, with the connection formed into a rounded shape. Optionally, a plastic deformable element is looped around at the end portion of the support and is used to form a second plastic deformable element. Additionally or alternatively, the element is repeatedly looped around at the ends of the support to form a plurality of plastically deformable elements. Optionally, the end portion in the plastically deformable element is formed into a circular loop at the end portion of the support. Optionally, a sleeve may be fitted over the end portion of the support for covering the end portion of the plastically deformable element.

In some embodiments of the present invention, the end portion of the support is configured at an angle for fitting over a proximal and/or a distal anastomosis. The angle ø may range from 20-80 degrees relative to the axis, for example from 20-40 degrees, from 20-55 degrees, from 20-65 degrees, and may optionally be 60 degrees. Optionally, an angular fitting with two openings, one on each end, is configured such that one opening is shaped at an angle for fitting over a proximal anastomosis, and the second end is shaped to be attached to the end portion of the support. Additionally or alternatively, an end portion of the support includes only elastically deformable elements which may be configured for fitting over the proximal anastomosis. The elastically deformable elements may be configured at an angle α which may range from 20-160 degrees relative to the longitudinal axis, for example from 20-60 degrees, from 60-90 degrees, from 90-120 degrees, from 120-150 degrees, and may optionally be 150 degrees.

According to an aspect of some embodiments of the present invention, there is provided a formable (shapeable) tubular support for longitudinal bodily vessels (e.g., blood vessels) that is capable of shaping and/or casting and/or contouring a vessel segment to an operator selected, or optionally predetermined, shape and/or course (direction). The term "tubular support" and "formable tubular support" may be used hereinafter interchangeably with "support", "vein support", and "shapeable support". The tubular support may optionally be used intraluminally (e.g., as an expandable stent) and may be provided in a vessel segment and once deployed, may be set to change current route and/or impose a specific chosen route. Alternatively or additionally, the intraluminal support can be selectively set to a different length and/or diameter, e.g., according sclerosis plaque length and/or target vessel diameter. In an exemplary embodiment of the present invention, the formable tubular support is an external stent or sheath that is first deployed to envelope the target vessel segment prior to optionally setting a desired course.

In some embodiments of the present invention, the shaping is accomplished by differentially and/or gradually pressing and/or securing a segmented vessel according to an operator determined fashion. Alternatively or additionally, the formable tubular support provides a substantially spacious frame that is malleable and/or plastically formable to a requested shape by the operator, into which a live tissue may grow until utilization of a framed space, while taking the general shape of the frame.

In some embodiments of the present invention, the formable tubular support is applied to support and/or optionally treat a locally damaged and/or diseased vessel (e.g., an occluded/stenotic blood vessel). In a second exemplary embodiment, the formable tubular support is used for supporting and/or optionally improving mechanical properties of a grafted vessel, harvested or synthetic.

The vessel segment may optionally be at least a small portion of the total vessel length, or may substantially encompass a full length of a vessel. In an exemplary embodiment of the present invention, the formable tubular support can be fitted to different lengths, either predeterminally or in-situ, and for example be cut-to-fit to the requested length and/or may be adjustably stretched accordingly.

In some embodiments of the present invention, the formable tubular support is capable of shaping and/or taking a shape in at least one dimension. Optionally, the formable tubular support is capable of maintaining a requested bent formation, alternatively or additionally a twisted formation, alternatively or additionally a curved formation of any kind. Optionally, the formable tubular support may be set to different three dimensional (3D) shapes. Optionally, the formable tubular support can be stretched to a requested length and substantially maintain it after removal of an elongating force. Optionally, the operator may adjust a chosen diameter and/or a peripheral shape of a specific vessel segment. Optionally, different shapes and/or diameters can be set along the vessel axis in contact with the formable tubular support.

In some embodiments of the present invention, the vein support is for protecting grafts from deformation such as kinking and for reducing or preventing restriction of blood flow in the graft. At least a portion of the support is made from a plastically deformable material so that the support may be shaped into a desired shape in which the support is stable in the body. The support may be used to impose a path on a grafted vein or artery in order to prevent or reduce deformation of the graft which might lead to kinking or folding and occlusion of the graft.

In some embodiments of the present invention, the vein support is deployed to support an anastomotic region, as for example in bypass surgeries. Optionally, the vein support supports at least part of a graft and at least one of its connection regions to a local bodily vessel. Optionally, the vein support includes a formable segment and a non-formable segment along its length. Optionally, at least part of the non-formable segment encircles the anastomosis region.

In some embodiments of the present invention, the plastically deformable material includes or is made of metallic material (e.g., stainless steel, Cobalt Chrome alloy, Aluminum, Titanium, etc.), optionally a polymer having plastic properties, optionally a putty-like modeling material, optionally a composite element that includes a plastically deformable matrix and/or binder materials. The material may include a combination of brittle and/or solid elements glued together by elastic fastening means. The material may include a non-setting adhesive or cement, optionally porous, which may optionally be applied in-situ (e.g., by spraying or other covering means).

In some embodiments of the present invention, the formable tubular support is provided as a spine-like element comprising a plastically deformable spine portion and a plurality of spaced apart extensions that are substantially tubular or can take a substantially tubular fashion in order to support a tubular bodily vessel. Optionally, at least one of the extensions is plastically deformable. Alternatively or additionally, at least one of the extensions is elastic (i.e., may substantially resume a former shape and/or diameter once an external unyielding force is removed).

In some embodiments of the present invention, the formable tubular support is provided as a mesh that includes at least one plastically deformable thread. The mesh may be braided, woven, knitted, pressed and/or in any other known construction and/or any combination thereof. The at least one thread may be a wire, a yarn, a filament a fiber, a rod, a stripe or any other longitudinal element having a relatively large length-to-diameter/width ratio; and may be made of any plastically deformable material, including but not limited to metal, polymers, composites, glued bundles, or any combination thereof.

In some embodiments of the present invention, the formable meshed support further includes at least one elastic member (either a thread or any other structural element) that provides elastic properties in at least one dimension. Optionally, the meshed support is plastically bendable and/or stretchable while maintaining elastic properties in at least a portion of its peripheral along its length (e.g., when compressed it will substantially resume its original peripheral shape, once the compressive force is removed). Optionally, the meshed support is a braided tubular support with at least one plastically deformable thread braided with at one elastically deformable thread.

In some embodiments of the present invention, the braided support is deployable as an external support to a blood vessel and/or a graft, and may be selectively transformed from a first compressed mode characterized by a large diameter, to a second stretched mode characterized by a smaller diameter, and vise versa. Optionally, while stretched or compressed, the braided support substantially preserves same or similar diameter-length ratio. Alternatively, there is no ratio and/or a fixed ratio between braid support's length and diameter, and any of these parameters may be set substantially independently. Optionally, the braided support can be stretched over at least part of the vessel/graft length until reaching a required diameter and/or length. In an exemplary embodiment, once stretched, the braided support substantially maintains its new length with minimal to no springback. Optionally, the braided support or a segment thereof can be substantially formable only after being set to a nominal stretched position. Optionally, the nominal stretched position is linked to a specific allowed/chosen springback value and/or to such a springback value. Optionally, the nominal stretched position is characterized by a braid angle of 0-180 degrees, optionally 10-100 degrees, optionally 25-60 degrees, or greater or lesser, or in-between.

In some embodiments of the present invention, at least one plastically deformable thread is interbraided in a tubular braided pattern further comprising at least one non-plastically deformable thread. Alternatively or additionally, at least one plastically deformable thread is wrapped around and over the tubular braided pattern. Optionally all plastically deformable threads are wrapped and/or interbraided in a single direction ("coiled formation"). Alternatively, at least two plastically deformable threads are wounded and/or interbraided in opposite directions ("braid formation").

In some embodiments of the present invention, the operator may choose to allow non-restrictive vessel/graft support by setting the second stretched mode to a diameter larger than vessel/graft outer diameter. Alternatively, the operator may choose to constrict or mechanically resist a possible expansion of the vessel/graft by choosing a diameter that is equal or smaller than vessel/graft outer diameter. According to design, the braided support can be fully restrictive (i.e., having solid properties not allowing radial expansion of the braid) or partially restrictive (i.e., having specific elastic/compliance properties). The braided support may include any combination of the above at different locations along its length. Optionally, the operator can now manipulate the braided support to a requested route that can be curved, bent, twisted or in any other variation.

In some embodiments of the present invention, specific braid pattern and/or threads parameters are chosen for a tubular blood vessel support to allow at least one of the following end points:

(1) in-situ formability of at least one support segment to a chosen fixed tubular and/or coaxial shape;
(2) in-situ formability of at least one support segment to a chosen fixed length;
(3) in-situ formability of at least one support segment to a chosen fixed diameter and/or a chosen fixed diameter slope;
(4) in-situ formability of at least one support segment to a chosen fixed course, while maintaining a substantially rounded contour;
(5) maintaining radial elasticity of at least one support tubular segment.

In some embodiments of the present invention, the formable tubular support is provided as a radially-collapsible support that can be sleeved over a vessel/graft while in expanded mode and then be set to a selected second collapsed mode (or alternatively may self-collapse to the second mode once a collapsing-resisting force is removed). Optionally, the support is set to be locked in the second mode formation. Optionally the support is so design to be selectively stretched up to a maximal length, with or without altering the support diameter. Additionally or alternatively, the support is shapeable and can be set to take specific form(s) as selected by operator. Optionally, the support includes at least one pre-set form that the operator can choose to set into. Alternatively or additionally, the support may be at least partially malleable and optionally may take complex forms chosen in-situ by the operator.

In some embodiments of the present invention, the formable tubular support is provided as a generally non-rigid tubular element with at least one plastically deformable joint, capable of bending and/or twisting. Optionally, the non-rigid element includes textile fibers (including but not limited to aramid/Dacron® fibers), optionally soft plastic/rubber, optionally nylon, optionally silicone. Optionally, at least one plastically deformable joint is fastened to a specific location along the tubular element periphery. Alternatively or additionally, at least one plastically deformable joint can be set to different positions along the tubular element by the operator. Optionally, at least one plastically deformable joint is a ring- or a bracelet-like element covering a portion of the non-rigid tubular element, which can set to move along the tubular element, optionally in a corresponding slot. Accordingly, the operator may cover a bodily vessel/graft with the formable tubular support and then place the at least one joint at a chosen location and bend it to a certain degree while altering the route of the non-rigid element and encompassed vessel/graft.

In some embodiments of the present invention, the formable support is provided as a tube and can only be pulled over (or under) the tubular bodily vessel or graft having at least one free end (i.e., prior to anastomosing). Alternatively, the formable support is opened along its length and can be closed over the bodily vessel/graft (e.g., similarly to a bracelet-cuff) using closing means, such as clips, hooks, adhesives, sewing means, zipping means, and/or may be deformably closed by applying enough force.

In some embodiments of the present invention, the formable tubular support is provided as plurality of coupling members or "building blocks" to modularly form a shaped tubular implant in-situ. Preferably, the coupling members are provided in different shapes, e.g., bent, curved and/or maintain any other non-tubular shapes, some may vary in diameter. Optionally, the operator may couple at least two coupling members over a target vessel/graft periphery and may choose specific shaped coupling members in order to set a specific chosen course. In this case, some or any of the coupling members may be rigid, elastic and/or plastic but may not be bounded to include plastically deformable members as previously described.

In some embodiments of the present invention, the formable tubular support includes at least one biodegradable and/or bioabsorbable element, e.g., magnesium, magnesium oxide, Polyglycolide (PGA), Polylactide (PLA), Poly(ε-caprolactone), Poly(dioxanone), Poly(lactide-co-glycolide), polyhydroxybutyrate (PHB) and polyhydroxyvalerate (PHV), etc.

In some embodiments of the present invention, the formable tubular support may be used in all types of bypass surgeries including cardiac and peripheral bypass procedures; as well as all kinds of surgical procedures that contain vascular anastomosis and/or reconstructions such as hepatic, renal, cardiac, pulmonary, intestinal transplantations and all kinds of vascular reconstruction procedures in which a portion of a vessel, or vessel anastomosis might be in jeopardy due to the reasons mentioned above. The vein support may also be beneficial in other vascular surgical procedures, and limb reconstructions or transplantations.

In some embodiments of the present invention, the formable tubular support comprises a sleeve having a lumen adapted to receive a vascular graft. Optionally, the support includes a spine and a plurality of looped extensions extending from the spine. Optionally, the support includes a braided or woven sleeve. Optionally, the support further includes a conical termination adapted for attachment to a body tissue. Optionally, the support is made from a biodegradable material, optionally configured to elute or contain a pharmacological substance.

In some embodiments of the present invention, the formable tubular support includes:
  (a) a first substantially tubular segment in contact with the bodily vessel and having a first longitudinal axis;
  (b) a second substantially tubular segment in contact with the bodily vessel and having a second longitudinal axis positioned in a first angle to the first longitudinal axis; and
  (c) at least one plastically deformable member engaged with the first and second substantially tubular segments, thereby allowing to selectively set a second angle between the first and second longitudinal axes.
Optionally, the selective setting changes the shape of the support and/or the shape of the bodily vessel. Optionally, the bodily vessel is an artery, a vein, or a graft. Optionally, the support is a stent, a meshed sleeve element, a spine-like element or a sheath element.

In some embodiments of the present invention, the formable tubular support externally supports the bodily vessel. Alternatively, the support internally supports the bodily vessel. Optionally, the first and second substantially tubular segments are interconnected. Optionally, the support includes a braided material with at least one plastically deformable thread. Optionally, the support further includes a plurality of elastic interlaced threads. Optionally, at least one thread is made from a biocompatible metal selected from the group consisting of Cobalt-Chrome alloy, Nitinol alloy, magnesium, magnesium alloy, tantalum and multiphase alloy. Alternatively or additionally, at least one thread is made from a biocompatible polymeric material selected from the group consisting of silicone, nylon, polyethylene, polyamide, aramid, polypropylene, PTFE and PET. Alternatively or additionally, at least one thread is made from a biodegradable material selected from the group consisting of magnesium oxide, Polyglycolide, Polylactide, Poly(ε-caprolactone), Poly(dioxanone), Poly(lactide-co-glycolide), polyhydroxybutyrate and polyhydroxyvalerate. Optionally, the support further includes at least one elastic member engaged with the first and second substantially tubular segments.

In some embodiments of the present invention, the formable tubular support is shaped as a curved tunnel, and/or as a straight tunnel and/or in a gradual decreasing diameter tunnel. Optionally, the support is plastically stretchable to a chosen length. Optionally, stretching the support will cause a decrease of an inner diameter thereof. Optionally, at least one of the substantially tubular segments is plastically stretchable. Optionally, stretching of one of the substantially tubular segments will cause a decrease of an inner diameter thereof.

In some embodiments of the present invention, the formable tubular support includes a plastically deformable member that is coiled over the substantially tubular segments. Optionally, the plastically deformable member is interbraidedly coiled around said substantially tubular segments. Alternatively or additionally, at least two plastically deformable members are coiled around the substantially tubular segments in opposite directions. Optionally, the plastically deformable member extends substantially along the support. Alternatively, the plastically deformable member extends along a portion of the support.

In some embodiments of the present invention, at least a portion of the support maintains radial elasticity. Optionally, at least a portion of the support resumes a substantially cylindrical shape after a non-circumferential external force is removed from its periphery. Optionally, the support substantially restricts radial expansion of at least a portion of the bodily vessel. Optionally, the support allows a radial expansion of at least a portion of the bodily vessel to a predetermined maximal diameter. Optionally, the support changes radial compliance of at least a portion of the bodily vessel, for example by substantially mimicking a predetermined value.

In some embodiments of the present invention a braided external support, includes:
  (a) a lumen adapted to receive a bodily vessel;
  (b) a plurality of interbraided elastic threads wounded around the lumen; and
  (c) at least one plastically deformable thread further interbraided with the elastic threads;
wherein the braided external support is adapted to reform into different substantially stable shapes.

In some embodiments of the present invention, a method of supporting a bodily vessel includes:
  (a) providing a support around the bodily vessel;
  (b) stretching the support over a portion of the bodily vessel; and
  (c) manipulating the support to alter the bodily vessel shape.

Optionally, the stretching is accomplished by applying opposite forces between two points along the support; wherein the stretching promotes a decrease of an inner diameter of the support between the two points. Optionally, the support is provided adjacent to anastomosed region of the bodily vessel. Optionally, the support is shaped as a curved tunnel and/or a straight tunnel and/or a gradually decreasing diameter tunnel. Optionally, step (a) further includes determining a course to the bodily vessel. Optionally, the shape substantially simulates said determined course.

In some embodiments of the present invention, the method of supporting a bodily vessel includes:
(a) providing a first external sleeve around a first portion of the bodily vessel;
(b) providing a second external sleeve around a second portion of the bodily vessel adjacent to the first portion; and
(c) circumferentially attaching in-situ the first and second external sleeves; wherein the first and second external sleeves differs in shape.

The inventors conducted a feasibility study including a CABG procedure on a sheep to evaluate the formable tubular support's positioning procedure; to evaluate safety of the support; and to evaluate the support's initial performance. The sheep was selected as its cardiovascular system is similar to that of humans; the sheep's growth rate is low comparing to other applicable models (e.g. swine model), allowing for a relatively long follow up period without substantial change in the size of organs; and the vein harvesting procedure is relatively easier and efficient compared to other applicable models. The support used was a cobalt chrome, biocompatible, braided support comprising 38 elastically deformable chrome wires of diameter 43 microns, and 4 annealed plastically deformable cobalt chrome wires of diameter 150 microns; the wires intertwined symmetrically into a braid structure. After a three month period following the CABG procedure involving the placement of the support, the sheep was scarified and the grafts and the heart harvested. Macroscopically, no damage to the heart was seen and the graft+ support system composite, like the rest of the operational field, was embedded in connective tissue and fat. The external support was fixed to the vein graft and was located exactly where it was positioned at the end of the surgery, with the same length and diameter.

The inventors further conducted testing to corroborate the length/diameter stability of the support and its capability to maintain a desired shape after being exposed to high pressure/high pulse physiological conditions. The testing included in vitro testing using plastic tubes through which water flowed to simulate arteries/veins with blood flow through them. Two different supports were tested, a first support comprising 38 cobalt chrome elastically deformable wires (50 microns diameter each) and 4 annealed plastically deformable cobalt chrome wires (150 microns diameter each); and a second support comprising 36 cobalt chrome elastically deformable wires (50 microns diameter each) and 6 annealed plastically deformable cobalt chrome wires (150 microns diameter each). The result of the in vitro tests showed no difference between the initial and final length of each support; that the supports can maintain their length/diameter and shape in relatively extreme physiological conditions; and that 4 annealed plastically deformable cobalt chrome wires may be used in lieu of 6 annealed plastically deformable cobalt chrome wires. Based on the results of the in vitro testing, the inventors have additionally determined that other suitable braided configurations for the support, which will provide higher radial compliance, may include a braid comprising 40 elastically deformable cobalt chrome wires of diameter 43 microns and 2 annealed plastically deformable cobalt chrome wires of diameter 150 microns, and a braid with the same number of wires as the first braid tested but with 4 annealed plastically deformable cobalt chrome wires of diameter 100-125 microns. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exemplary Plastically Deformable Vessel Supports

Figure 1B:
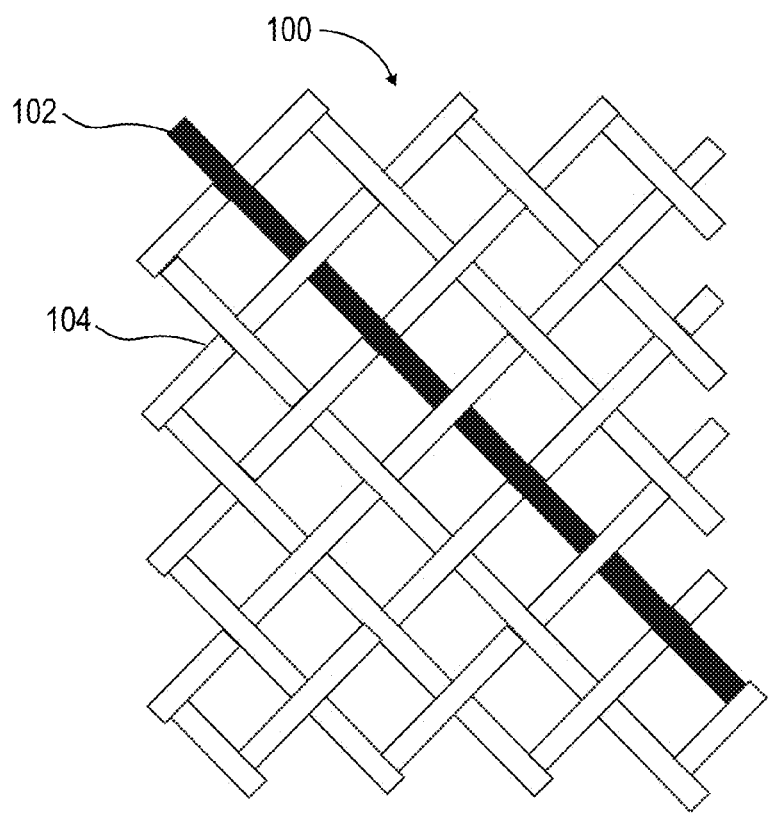
FIG. 1B schematically illustrates an enlarged view of a braided plastically deformable fiber and a plurality of deformable fibers in the vein support of FIG. 1A, in accordance with an embodiment of the present invention.

Referring now to the drawings, FIG. 1A schematically illustrates an isometric view of an exemplary vein support 100, in accordance with an embodiment of the present invention. Reference is also made to FIG. 1B which schematically illustrates an enlarged view of a braided (interlaced/interwoven) plastically deformable fiber 102 and a plurality of deformable fibers 104 in support 100, in accordance with an embodiment of the present invention. Vein support 100 supports body vessels such as, for example blood vessels (not shown), wherein the support may be fixedly displaced relative to an axis 108 by plastic deformation of the support relative to the axis. Support 100 may be plastically stretched along axis 108, and may be additionally compressed along the axis, with minimal or optionally, no springback. Optionally, support 100 may be axially bent (by applying a force with a component perpendicular to axis 108) and/or may be twisted about the axis, with minimal or optionally no springback. That is, elastic forces acting on support 100 to return it to its previous shape (prior to stretching, compressing, bending, or twisting, or any combination thereof) are minimal and the support substantially maintains the new shape.

In some embodiments of the present invention, vein support 100 includes a diameter d which may be variable and fixedly deformed along axis 108. Optionally, different segments of the support may be manipulated to have different diameters. Fixedly deforming diameter d along axis 108 allows for an operator to adjust different segments, points or sections of the support to a varying cross-sectional diameter of the vessel, thereby providing a more uniform support and sheathing of substantially uniform as well as substantially non-uniform vessels.

Optionally, support 100 may include a radially elastic portion along a length of support 100. Radial elasticity allows the segment to regain its fixedly deformed diameter despite application of a compressive force at one or more points along a circumference of the segment (once the compressive force is removed, the segment returns to the fixedly deformed diameter and does not remain deformed due to the applied force). A potential benefit of radial elasticity is that the vessel may return to its original shape once the compressive force is removed, and does not remain "pinched" by a permanent deformation of support 100. In some embodiments, the radial elasticity may decrease as the diameter of the segment decreases and a length of support 100 increases. Optionally, an elasticity of the portion increases as the support increases in length and diameter d decreases.

Support 100 may be a braided tubular body having a lumen 106 extending from a proximal end to a distal end (also from distal end to proximal end), and includes at least one plastically deformable element which may be, for example, plastic deformable fiber 102. As shown in the figure, support 100 includes a plurality of fibers 102, which are shown helically (spirally) wound along the length of the support, some in a clockwise direction, and others in a counterclockwise. Optionally, fiber 102 may helically wind along the length of support 100 from one direction, clockwise or counterclockwise. Support 100 may include a plurality of deformable elements such as, for example elastic fibers 104, which may be interlaced with plastic deformable fiber 102. Optionally, fibers 102 may be interlaced with other plastic deformable fibers.

Fiber 102 may be made from any plastically deformable material including but not limited to metal, stainless steel or plastic. Fiber 104 may be plastically deformable, elastically deformable, super-elastically deformable, or may posses any other non-rigid property. Optionally, fibers 102 and 104 are made from a same material but posses different mechanical properties (e.g., plastic vs. elastic properties) due to different material preparations. For example, in some embodiments, fiber 102 may be an annealed metallic fiber and fiber 104 may be a cold-worked metallic fiber. Optionally, fiber 102 and/or 104 may include biocompatible metals, e.g., biocompatible super alloys, and/or are selected from a group consisting of Cobalt-Chrome alloy, Nitinol alloy, magnesium, magnesium alloy, tantalum, multiphase alloy (e.g., MP35N), or any combination thereof. Optionally, fiber 102 and/or 104 may include biocompatible polymeric materials and/or are selected from a group consisting of silicone, nylon, polyethylene (e.g., Dyneema® or Spectra®), polyamide/aramid (e.g., Kevlar®), polypropylene, polytetrafluoroethylen (PTFE), Polyethylene terephthalate (PET), or any combination thereof. Optionally, fiber 102 and/or 104 are biodegradable and/or bioabsorbable materials, and/or are selected from a group consisting of magnesium oxide, Polyglycolide (PGA), Polylactide (PLA), Poly(ε-caprolactone), Poly(dioxanone), Poly(lactide-co-glycolide), polyhydroxybutyrate (PHB), polyhydroxyvalerate (PHV), or any combination thereof.

In some embodiments of the present invention, support 100 may externally cover and support a body vessel, which may be a graft, while maintaining its shape. Optionally, support 100 may be used as a sheath to wholly, or optionally partly, constrict a radial expansion in the vessel. Optionally, the radial expansion is limited to a predetermined maximum diameter. Additionally or alternatively, support 100 may be used to wholly, or optionally partly, restrict kinking in the vessel. Optionally, support 100 may be used to add to the vessel's radial compliance, which is given by a ratio of a diameter change of a vessel as it expands in a radial direction in response to a given change in vessel pressure. Additionally or alternatively, support 100 may support the vessel under systolic and/or diastolic and/or under peak and/or pulsative pressures of 400 mmHg or less, optionally 200 mmHg or less.

In some embodiments of the present invention, plastically deformable fiber 102 is configured to enable support 100 to be plastically deformed by the operator and manipulated into a required fixed shape. Optionally, support 100 may be manipulated by the operator to accommodate for a vessel to follow over a specific path inside a body (not shown) to a target vessel (that to which a distal end of a vessel is being attached by anastomosis), and/or to accommodate to a shape of the target vessel. Optionally, the operator may stretch support 100 before or after covering the target vessel until reaching a required length and/or a maximal allowed length. Optionally, stretched support 100 substantially maintains a stretched length under similar pressure regimes as described above. Optionally, when longitudinally stretching support 100 between two particular points along axis 108, a diameter d of the segment of the support between the points decreases. Optionally, when compressing support 100 longitudinally between two points along axis 108, diameter d increases in the segment between the two points.

In some embodiments of the present invention, plastic deformation of support 100 is determined by a braiding angle formed by a diagonal intersection of a first and second plastically deformable fibers 102 (e.g., angle θ shown in FIG. 11D), the braiding angle associated with a nominal length of the support. As support 100 is stretched braiding angle θ decreases, increasing the axial plasticity of the support, and optional its radial elasticity, That is, for a braiding angle greater than a maximal braiding angle, for example 150 degrees when an average diameter d in support 100 is approximately 8 mm (the angle may also be indicative of the support being below the nominal length), the support is acted upon by elastic forces preventing the support from being fixedly displaced relative to axis 108 (the support does not necessarily maintain the shape). For a braiding angle lesser than a minimal braiding angle, for example 71.4 degrees where diameter d in support 100 is reduced to below 5 mm, (see Table-1 further on below in section Examples) (the angle may also be indicative of the support being above the nominal length), the plastically deformable fibers 102 are much more dominant in the longitudinal length, resulting in an overall greater plasticity of support 100 relative to its axis 108, as previously described. Optionally, the nominal length is characterized by a braid angle ranging between 0-180 degrees, for example, 10 degrees, 30 degrees, 45 degrees, 60 degrees, 90 degrees, 120 degrees, 150 degrees.

A principle of the design is to have a good tradeoff between minimal determination, selecting a combination of plastic fibers and elastic members having a defined number of fibers, a defined diameter, heat treatment conditions, interlacing combination, among other characteristics as described below. For example, as previously described, the fibers may be from cobalt-chrome. Plastically deformable fiber 102 may then be annealed so as to give the fibers their plastic deformable characteristics. Non-plastically deformable fiber 104 may be cold worked so as to give the fibers their elastic characteristics.

In some embodiments of the invention, springback from stretching support 100 may range from 0.5%-50%, for example, 0.5%-5%, 2%-10%, 2%-20%, 2%-30%, 2%-40%, Optionally, springback in radial elasticity may range from 2% to 50%, for example, 2%-5%, 2%-10%, 2%-20%, 2%-30%, 2%-40%, In some embodiments of the present invention, plastically deformable fiber 102 may have an average diameter in the range of 20 to 1,000 μm, optionally between 50 to 200 μm, optionally approximately 75 μm, optionally approximately 150 μm. Optionally, fibers 104 are elastic and have an average diameter in the range of 10 to 500 μm, optionally between 20 to 100 μm, optionally approximately 43 μm.

In some embodiments of the present invention, support 100 includes at least 4 fibers, optionally 10-20 fibers, optionally 20-50 fibers, optionally 50-100 fibers, optionally 100-200 fibers, optionally more than 200 fibers. Optionally, support 100 includes less than 4 fibers. Optionally, support 100 includes one or more fibers 102, for example 1-10 fibers, 1-20 fibers, 1-50 fibers, 1-100 fibers, or more. Optionally, support 100 includes at least one fiber 102, for example 1-10 fibers, 1-20 fibers, 1-50 fibers, 1-100 fibers, 1-500 fibers, or more.

In some embodiments of the present invention, support 100 may include 36, 42 or 48 fibers, out of which 4, 6 or 8 are plastically deformable fibers 102 having a diameter in a range of 75-150 μm, and the remaining fibers are fibers 104 having a diameter in a range of 25-75 μm. Optionally fibers 102 and/or 104 have a relatively circular cross section, optionally polygonal, optionally flat, or any combination thereof.

In some embodiments of the present invention, support 100 includes a pre-stretched (prior to plastic deformation along axis 108) length in a range of 5 to 1,000 mm, optionally 30 to 500 mm, optionally 50 to 100 mm. Optionally, support 100 includes a pre-stretched length less than 10 mm. Optionally, a pre-stretched diameter d may be in a range between 1 to 80 mm, for example 4 to 30 mm, 5 to 10 mm, and may be constant along the pre-stretched length of the support. Optionally, diameter d decreases in relation to the braid angle. Optionally support 100 may be stretched (plastically deformed) until reaching a minimal diameter of 1 to 40 mm, optionally 1 to 5 mm, optionally 3-4 mm. Optionally, in the pre-stretch length, the braid angle may range from 50 to 200 degrees, optionally 120 to 180 degrees, or higher or lesser or intermediate. Optionally, support 100 may be stretched until the diameter d averagely decreases to between 1 mm-15 mm, for example, 8 mm, 6 mm, 4 mm, or 2 mm.

In some embodiment of the present invention, support 100 may be configured for use in peripheral vein grafts, which may substantially differ from coronary vein grafts with increased length and diameter and more significant diameter change along its length. Optionally, Support 100, at stretched out length, may range from 10 mm to 2,000 mm, for example, 50 mm-1,500 mm, 100 mm-1,000 mm, 300 mm-800 mm, 400 mm-600 mm. In peripheral vein grafts, support 100 may include a diameter which, following stretching out of the support, may range from 3 mm-12 mm, for example 5 mm-9 mm. Optionally, support 100 may be tapered so that a proximal end has a larger diameter than a distal end following stretching out. Optionally, the distal end may have a greater diameter than the proximal end.

In some embodiments of the present invention, an axial stiffness and/or radial force of support 100 varies when stretched or compressed. Optionally, axial stiffness at different stretching positions is in the range of 0.1 to 30 N/m, optionally between 0.3 to 20 N/m. Optionally, the axial stiffness is 0.4-1 N/m, optionally about 0.6 N/m, when support 100 is fully compressed and/or its diameter is 5 to 10 mm, optionally about 8 mm. Optionally, the axial stiffness is 10-20 N/m, optionally about 15 N/m, when support 100 is fully mode and/or its diameter is 1 to 5 mm, optionally about 3 mm.

Shown below in Examples is Table-1 which shows calculated diameters, lengths, braid angles and axial stiffness properties, at different stretching positions, for a support comprising 38 elastic fibers of 0.05 mm in diameter, braided on an 8 mm mandrel and using 150° braiding angle, in accordance with an embodiment of the present invention.

Reference is now made to FIGS. 2, 3 and 4 which schematically illustrate exemplary vein supports 200, 300 and 400 respectively, in accordance with some embodiments of the present invention. Supports 200, 300, and 400 are similar to support 100 shown in FIG. 1, with a difference that a tubular body of each support includes a different braiding pattern.

As shown in FIG. 2, support 200 includes a plurality of plastically deformable fibers 202 helically winding in a counterclockwise direction along the length of the support, in a general direction parallel to axis 208. Optionally, fiber 202 may helically wind in a clockwise direction along the length of support 200. Support 200 includes a plurality of non-plastic deformable elements such as, for example deformable fibers 204, interlaced with plastic deformable fiber 202 to form the braided tubular body. Optionally, fiber 202 may be interlaced with other plastic deformable fibers. Fiber 202 and fiber 204 may be substantially the same as fiber 102 and fiber 104 shown in FIG. 1.

As shown in FIG. 3, support 300 includes a single plastically deformable fiber 302 extending along the length of the support parallel to axis 308. Optionally, support 300 may include a plurality of fibers 302 extending along the length of the support parallel to axis 308. Support 300 includes a plurality of non-plastic deformable elements such as, for example deformable fibers 304, interlaced with plastic deformable fiber 302 to form the braided tubular body. Fiber 302 and fiber 304 may be substantially the same as fiber 102 and fiber 104 shown in FIG. 1.

As shown in FIG. 4, support 400 includes a plurality of plastically deformable fibers 402, some helically winding in a counterclockwise direction and some in a clockwise direction, along the length of the support, in a general direction parallel to axis 408. Support 400 includes a plurality of non-plastic deformable elements such as, for example deformable fibers 404, interlaced with plastic deformable fiber 402 to form the braided tubular body. Optionally, fiber 402 may be interlaced with other plastic deformable fibers. Fiber 402 and fiber 404 may be substantially the same as fiber 102 and fiber 104 shown in FIG. 1.

Figure 5A:
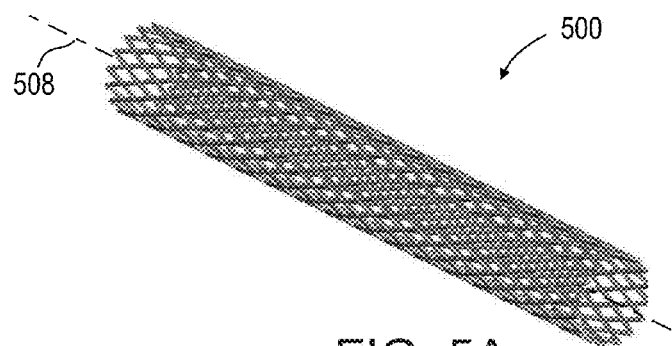
FIG. 5A schematically illustrates an exemplary formable stent, in accordance with some embodiments of the present invention.
Figure 5B:
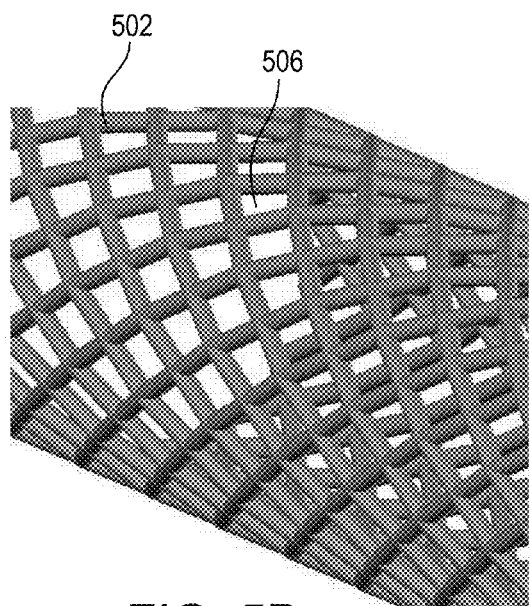
FIG. 5B schematically illustrates an enlarged view of a section of the stent of FIG. 5A, in accordance with some embodiments of the present invention.

Reference is now made to FIG. 5A which schematically illustrates an exemplary formable support 500, and to FIG. 5B which schematically illustrates an enlarged view of a section of the support, all in accordance with some embodiments of the present invention. Support 500 may be any metal or polymeric support that can be shaped in at least one axis, including but not limited to an axis 508, radial axis or any combination thereof, and/or may be curved and/or bent and/or twisted and/or be selectively locked, at least partially, in a specific form chosen by an operator. Optionally, Support 500 is an intraluminally radially-expandable support and/or an extraluminally radially-collapsible support. Optionally, a diameter (not shown) of support 500 may be selectively varied by the operator, optionally gradually. Optionally, support 500 is self-expandable (held compressed and expands when released) or collapsible after deployment. Optionally, support 500 may be manually expandable and/or balloon expandable. Optionally, support 500 may be plastically deformed to a required length. Optionally, support 500 includes a diameter which decreases when the support stretches along/relative to axis 508.

In some embodiments of the present invention, support 500 may be a braided support including at least one plastically deformable strut 502. Optionally, struts 502 may define openings 506 that can be of any shape, including but not limited to polygonal shapes, optionally quadrangular. Optionally, struts 502 may include similar plastically deformable characteristics to those of fiber 102 shown in FIG. 1. Additionally or alternatively, support 500 may include any other type of support, including but not limited to bare metal/polymeric support, drug eluting support that may or may not be produced by one of more of the followings methods; laser cutting, EDM, chemical etching, micromachining, photo-etching and waterjet laser cutting.

Figure 6:
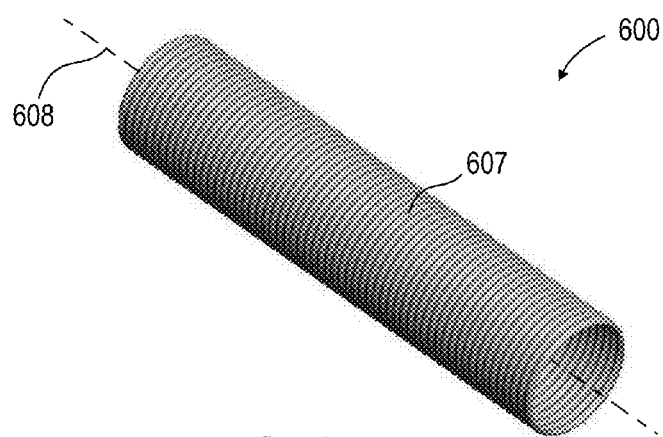
FIG. 6 schematically illustrates a formable bellows cover support having a plurality of rings, in accordance with some embodiments of the present invention.

Reference is now made to FIG. 6 which schematically illustrates a formable bellows cover support 600 having a plurality of rings 607, in accordance with some embodiments of the present invention. Optionally, bellows 600 are plastically deformable and can maintain any curved and/or bent shape as described in this disclosure. Optionally, bellows 600 are stretchable and can maintain a chosen length along axis 608.

Exemplary Method of Treatment

Figure 7A:
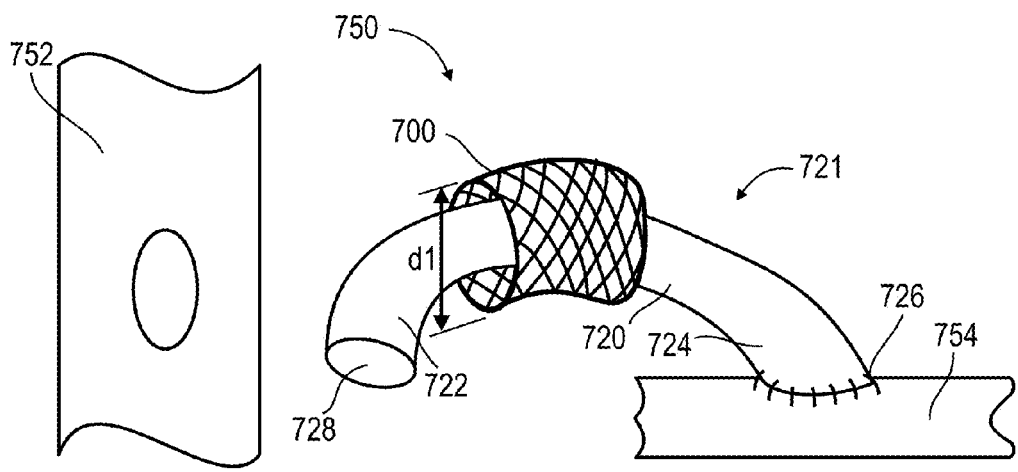
FIGS. 7A-7C schematically illustrate a method of using a vein support in a vein-based bypass operation, in accordance with an embodiment of the present invention.
Figure 7B:
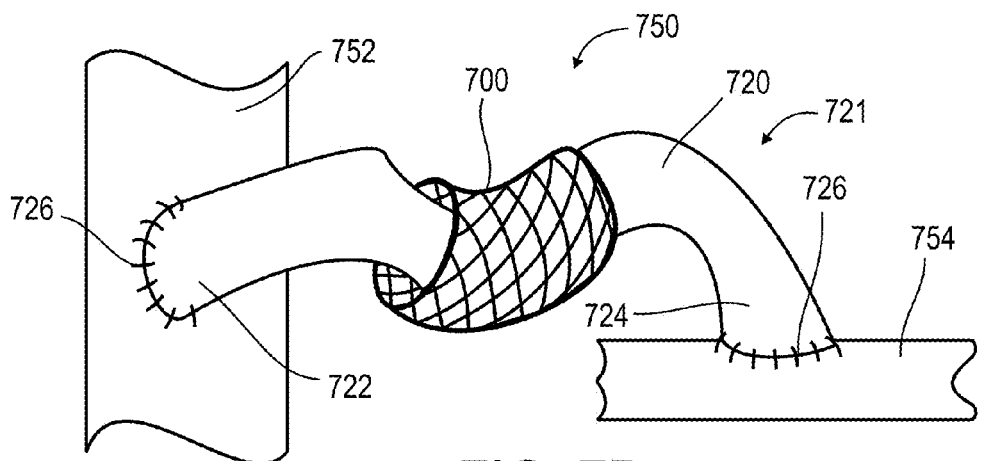
Figure 7C:
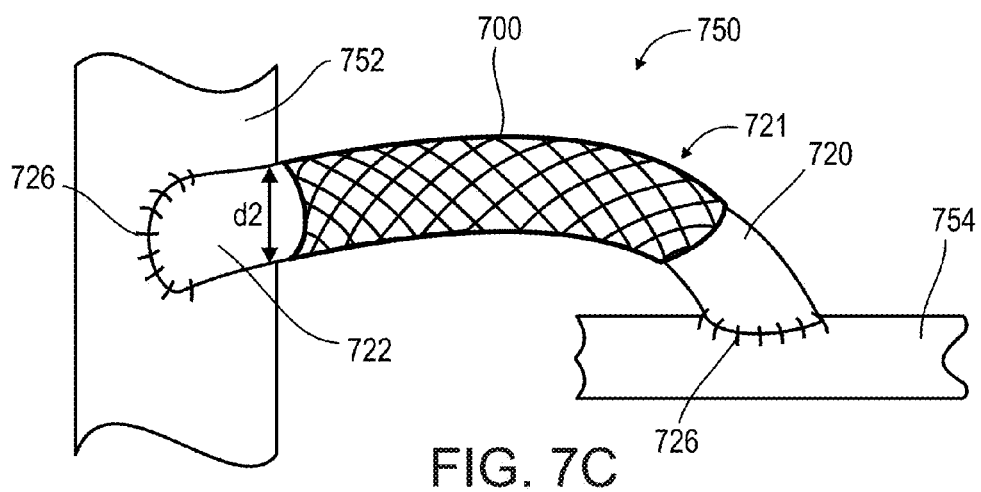

Reference is now made to FIGS. 7A-7C which schematically illustrate a method of using a vein support 700 in a vein-based bypass operation, in accordance with an embodiment of the present invention. It should be evident to an ordinary person skilled in the art that the method described is not intended to be limiting in any way, and that there are many other ways of implementing the method. Furthermore, the vein-based bypass operation may refer to any type of operation comprising a vascular graft. Vein support 700 may be the same as vein support 100 shown in FIG. 1. Optionally, vein support 700 may be the same as that shown in FIG. 2, 3, 4, 5A, or 6 at 200, 300, 400, 500, or 600, respectively.

In general, deployment of support 700 may be performed in-situ during a bypass surgery, such a CABG surgery, or in any other surgical intervention. Optionally, support 700 may be deployed in an open surgery with or without a heart-lung machine. Alternatively, support 700 may be deployed minimally invasively and/or percutaneously. Optionally, a special delivery device (not shown) may be used to introduce support 700 into a body and/or to deploy the support over a target graft or vessel segment and/or to stretch at least part of the supporting element to a chosen length, and/or to shape, contour and/or cast the graft/vessel in a required shape by altering the support. Alternatively or additionally, support 700 may be introduced manually, for example in an open surgery. Optionally, support 700 may be sleeved over a vessel while in a first larger minimal diameter later to be optionally set to a second smaller minimal diameter. Optionally, the supporting element may include a distal end that is wider than the average diameter of the supporting element, which may serve as a leading edge for sleeving over a vessel.

Graft 721 includes a graft body 720 having a first end 724, a second end 722 and a lumen 728. Optionally, graft 721 is a bypassing channel being anastomosed during a bypass surgery to internal organs 750 that include first and second bodily vessels 752 and 754. Optionally, the bypass surgery is a CABG surgery. Optionally, graft 721 is a saphenous vein graft although it can be any type of autologous or donor or synthetic graft. Optionally, the first and second vessels 752 and 754 are arteries, or alternatively veins.

FIG. 7A shows a first step of placing support 700 over graft 721, wherein the support is compressed (pre-stretched) and/or provided compressed with a diameter d1 that is substantially larger than the grafts outer diameter. Optionally, diameter d1 is over 3 mm, optionally over 7 mm, or higher or lower or intermediate. Preferably, support 700 is deployed after one end of graft 721 (e.g., first end 724) is connected to one bodily vessel (e.g., first vessel 754) via a first anastomosis 726.

FIG. 7B shows a second step, in which a second end 722 of graft 721 is connected to second bodily vessel 752 via anastomosis 726, thereby connecting the interiors of bodily vessels 752 and 754 through graft lumen 728. Optionally, graft 721 is in an undefined contour that can optionally be determined according to blood pressure and flow regimes, properties of graft 721 that may include its mechanical properties, dimensional properties and weight, and/or other parameters.

FIG. 7C shows a third step, in which support 700 is in stretched mode and having a second diameter d2, which is optionally different to diameter d1. Adjusting a shape of support 700 to support and accommodate graft 721 is optionally done following restoration of blood flow through the graft. Optionally, diameter d2 is smaller than 8 mm, optionally smaller than 5 mm. Optionally, support 700 is stretched to substantially contact graft 721 along at least part of its length. Optionally, support 700 or a segment of it is further stretched to further decrease a smaller diameter, thereby constricting the graft 721 segment in contact. Alternatively or additionally, at least one segment along support 700 is set to have a diameter that is larger than its corresponding enveloped graft 721 segment, thereby allowing it to expand (if in a cyclic expansion pattern and/or in a progressed expansive remodeling). Optionally, at least one of the anastomosed ends and/or its close-by surroundings are covered and/or supported by at least part of support 700 (not shown). Optionally, once deployed, support 700 can then be manipulated to adjust a chosen contour to at least part of the covered segment of graft 721. Optionally, support 700 fully stretched is firm enough to substantially maintain the applied contour either permanently or for a prolonged period of time after end of the surgical procedure, optionally over 1 week, optionally over 1 month, optionally over 1 year, optionally over 10 years, or higher or lesser or intermediate.

Figure 8A:
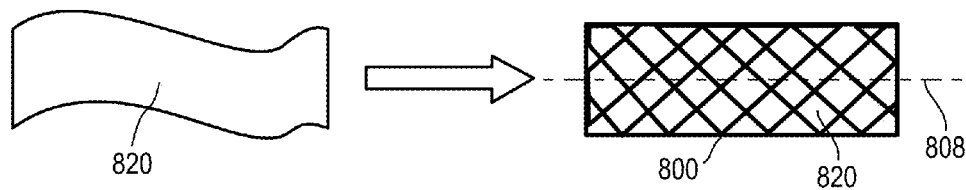
FIGS. 8A-8C schematically illustrate side views of different supporting patterns for several exemplary graft segments, using a vein support, in accordance with some embodiments of the present invention.
Figure 8B:
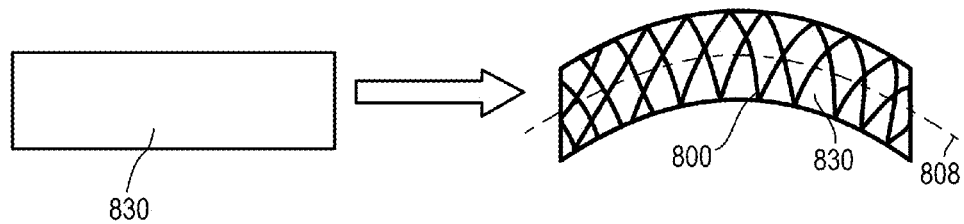
Figure 8C:
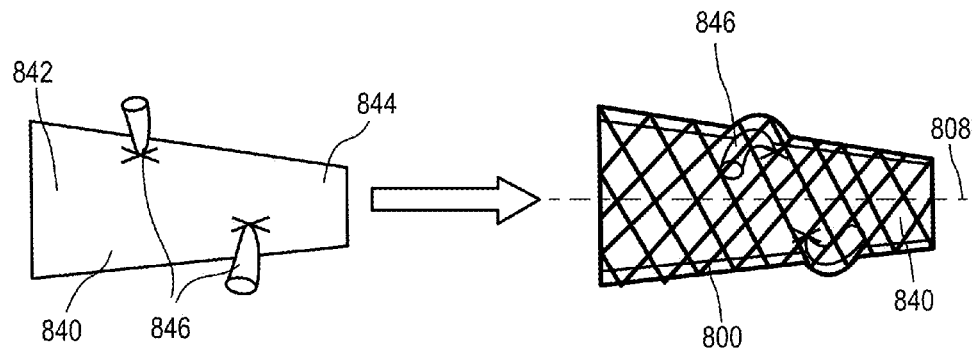

FIGS. 8A-8C schematically illustrate side views of different supporting patterns for exemplary graft segments 820, 830 and 840, respectively, using a vein support 800, in accordance with some embodiments of the present invention. Vein support 800 may be the same as vein support 100 shown in FIG. 1. Optionally, vein support 700 may be the same as that shown in FIG. 2, 3, 4, 5A, or 6 at 200, 300, 400, 500, or 600, respectively. It should be evident to an ordinary person skilled in the art that the exemplary graft segments shown are not intended to be limiting in any way, and that there are many other types of graft segments and ways in which support 800 may be to support the segment.

In FIG. 8A, support 800 is used to straighten an undefined contour of graft segment 820, support plastically deformed along an axis 808 of the support. In FIG. 8B, support 800 is used to apply a selected curvature to a straight graft segment 830, the support plastically deformed in a direction transversally to the axis 808. In FIG. 8C, support 800 is used to support graft segment 840 without significantly altering its direction and/or shape. As illustrated, graft segment 840 includes two opposite ends 842 and 844 substantially differentiated in diameter. Optionally, graft segment 840 is conically shaped wherein a diameter of end 842 diameter is substantially larger than a diameter of opposite end 844. Optionally, graft segment 840 includes at least one collateral 846. In order to provide support along most or all of graft segment 840 length, support 800 is stretched in a gradual manner along axis 808 to produce a corresponding conically pattern over the graft segment, with optional bumps for covering collaterals 846.

Exemplary In-Situ Assembly of a Modular Vessel Support

Figure 9A:
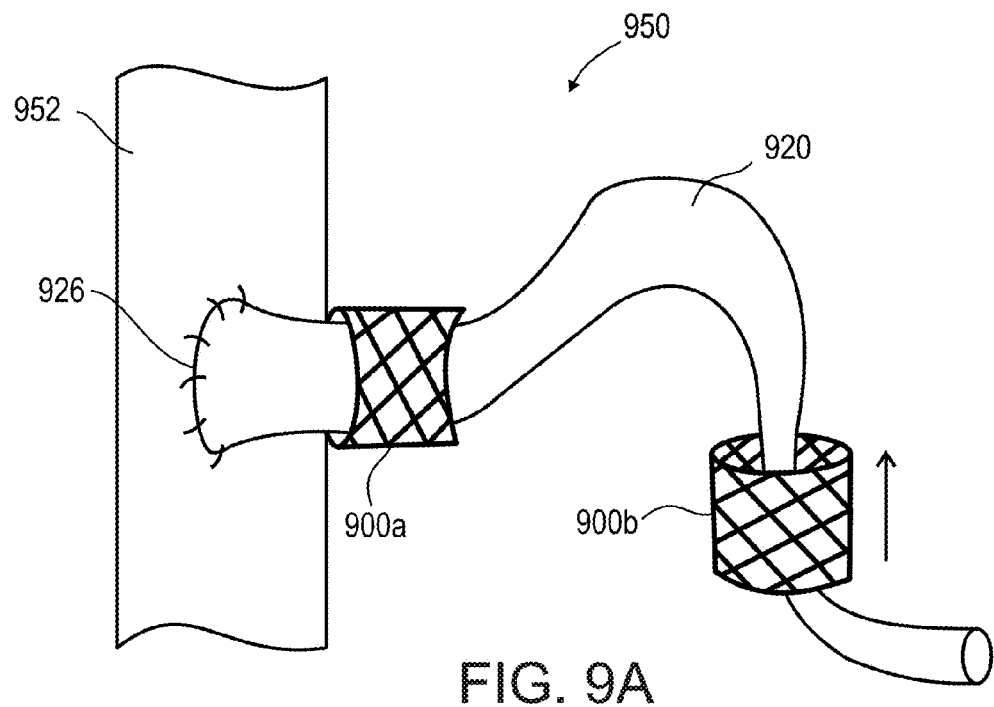
FIG. 9A schematically illustrates an exemplary loose bodily vessel having a first free end and a second end connected to an artery of an internal organ, in accordance with some embodiments of the present invention.
Figure 9B:
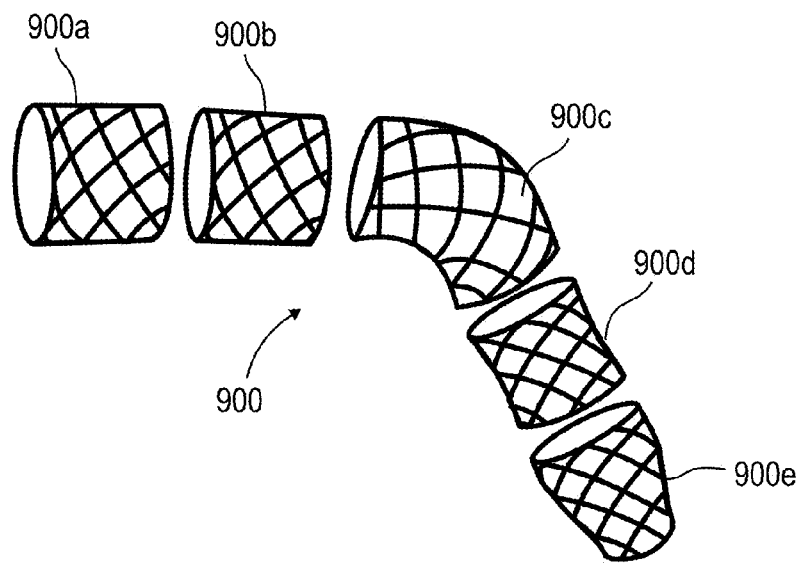
FIG. 9B schematically illustrates a modular vein support, in accordance with some embodiments of the present invention.

Reference is now made to FIG. 9A which schematically illustrates an exemplary loose bodily vessel 920 having a first free end and a second end connected to an artery 952 of an internal organ 950, and to FIG. 9B which schematically illustrate a modular vessel support 900, all in accordance with some embodiments of the present invention. Optionally, vessel 920 is connected to artery 952 with an anastomosis 926.

In accordance with some embodiments of the present invention, a support link 900a included in modular support 900 is secured over a segment of vessel 920, as illustrated in the figure. Optionally, support link 900a is a tubular braided body similar to any one of the supports previously described, for example support 100, support 200, support 300, or support 400. Optionally, support link 900a is a support element as exemplary support 500 shown in FIG. 5, or optionally exemplary bellow 600 shown in FIG. 6. Optionally, support link 900a is a spinal support as an exemplary graft casting device described further on below, or any other support or sheath type or generally tubular member. Optionally, support link 900 is plastically deformable, or is elastic, or includes any variation thereof. Optionally, support link 900a is substantially rigid. Support link 900a is secured to vessel 920 either by reshaping it to coincidentally cover and/or constrict a segment of vessel 920, or by any other connecting means and/or adhesive materials.

In some embodiments of the present invention, support link 900a is a section of modular support 900 which may be assembled in-situ over vessel 920. Alternatively, a part of modular support 900 may be assembled outside a body prior to implantation. As shown in FIG. 9A, a second support link 900b is advanced over vessel 920 towards link 900a, illustrating an optional step in assembling modular support 900 in-situ.

Modular support 900 includes a plurality of interconnected links such as 900a, 900b, 900c, 900d and 900e. Optionally, modular support 900 is a part of a larger modular support containing more support links (not shown). In an exemplary embodiment, at least two links are provided in different tubular shapes. For illustrative purposes only, links 900a, 900b and 900d can be provided substantially cylindrical, whereas link 900c is provided as curved or bent tube and link 900e is provided as a converging (e.g., bell-shaped) tube. Optionally, at least one link is substantially rigid and maintains its provided shape under reasonable applied forces. Alternatively or additionally, at least one link is substantially elastic and/or resiliently flexible and is capable of regaining, spontaneously or with moderate urging, to its nominal (e.g., provided) shape. Alternatively or additionally, at least one link is at least partially plastically deformable in at least one axis. Optionally, at least one link includes a tubular braid body and includes at least one plastically deformable wire and/or at least one elastic or resiliently flexible wire. In an exemplary embodiment of the present invention, an operator is provided with a kit containing plurality of links that can be assembled to a modular support, such as modular support 900, in a one of several possible shapes and/or contours and/or courses chosen by the operator.

Exemplary End Portions of a Vessel Support

Figure 10A:
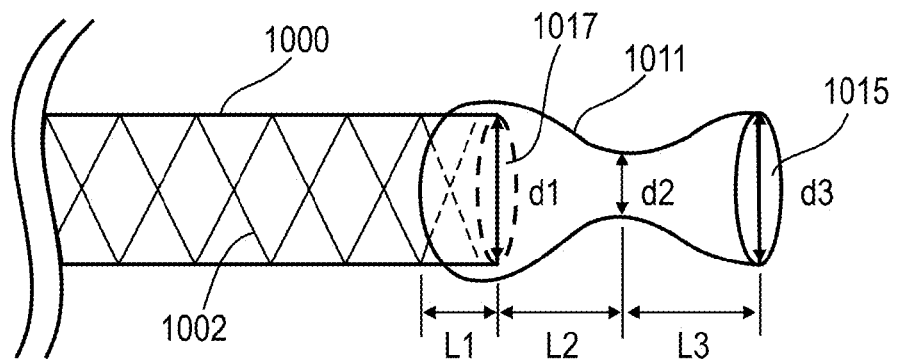
FIGS. 10A-10C schematically illustrate exemplary coverings and/or sleeves applied to an end portion of a vein support, in accordance with some embodiments of the present invention.
Figure 10B:
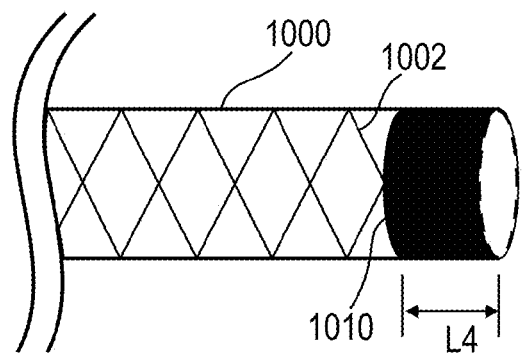
Figure 10C:
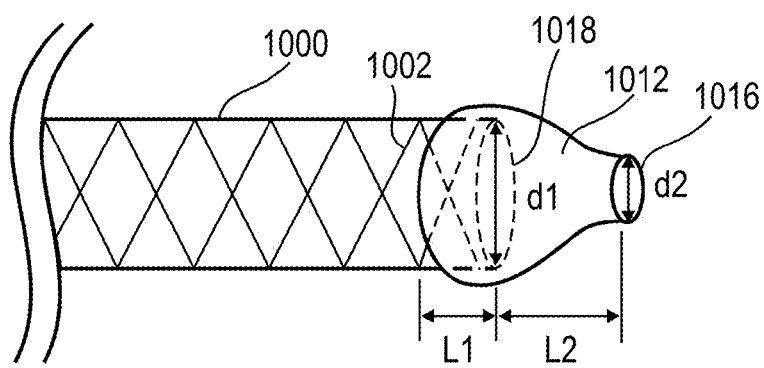

Reference is made to FIGS. 10A, 10B and 10C which schematically illustrate exemplary coverings and/or sleeves applied to an end portion of a vein support 1000 optionally intended for covering an anastomosed area, in accordance with some embodiments of the present invention. It is suggested that special attention should be made to support end portions design, since that the intersection between a graft vessel and its anastomosed counterpart is occasionally angular and/or irregular. Vein support 1000 may be the same as vein support 100 shown in FIG. 1. Optionally, vein support 1000 may be the same as that shown in FIG. 2, 3, 4, 5A, 7A, 8A, or 9B at 200, 300, 400, 500, 700, 800 or 900, respectively.

In some embodiments, support end portion is plastically deformable relative to an axis and/or includes at least one plastically deformable member (e.g., a thread). Alternatively, support end portion is substantially elastic as to allow a relatively "soft" covering while excluding the need to cast a requested shape. Occasionally, plastically deformable fibers, such as that shown in the figures at 1002, may include end portions which protrude from an end portion of support 1000 and impose a degree of overall plasticity to its corresponding support segment. Alternatively or additionally, such protruding fiber end portions may pose a potential risk of injury to a body organ or a vessel due to prickling or piercing. Optionally, a sleeve or a cover may be used at the end portion of the support to cover protruding fibers and thereby substantially prevent possible injury.

FIG. 10A shows a sleeve 1011 which may be attached through a first opening 1017 to the end portion of support 1000 and through an opposing second opening 1015 to an anastomosed area. Opening 1017 may be of an internal diameter d1, for example 8 mm, suitable for fitting the end portion of support 1000 (in an optional pre-stretched form) along a distance L1, which may range, for example between 2 and 5 mm, inside the sleeve. Opening 1015 may be of a diameter d3 suitable for fitting the anastomosis up to a distance L3, for example 10 mm, into the sleeve, depending on a diameter of the anastomosis. Optionally, if a diameter of the anastomosis is less than a diameter d2 which may be, for example 5 mm, separating opening 1015 from opening 1017, the anastomosis may be inserted an additional distance L2, which may be for example 10 mm, until an edge of the end portion (although very close to the edge may result in injury from fiber 1002). Sleeve 1018 may be made from a smooth, flexible material, such as, for example, silicon. FIG. 10B is an alternative exemplary embodiment showing an end portion of support 1000 with a covering 1010 including a coating of a flexible material, for example silicon, which may cover the end portions of fibers 1002 so as to substantially prevent possible injury, and sufficiently elastic to allow movement of the coated fibers. Optionally, the coating may have a thickness ranging from 10-100 microns, and may extend along a length L4 of the end portion, optionally from 2 to 5 mm.

FIG. 10C is yet another exemplary embodiment showing a sleeve 1012 similar to sleeve 1017 in FIG. 10A with a difference that sleeve 1012 may be configured to attach to a relatively smaller diameter anastomosis through a second opening 1016 which may have a diameter d2 similar to diameter d2 in sleeve 1011. Sleeve 1012 may attach to the end portion of support 1000 by a first opening 1018 which may have a diameter d1 similar to d1 in sleeve 1011. Lengths L1 and L2 may be similar to that in sleeve 1011.

Reference is made to FIGS. 11A, 11B, 11C and 11D showing exemplary end portion designs of a vein support 1000 optionally intended for covering an anastomosed area, in accordance with some embodiments of the present invention. Vein support 1100 may be the same as vein support 100 shown in FIG. 1. Optionally, vein support 1100 may be the same as that shown in FIG. 2, 3, 4, 5A, 7A, 8A, or 9B at 200, 300, 400, 500, 700, 800 or 900, respectively.

Figure 11A:
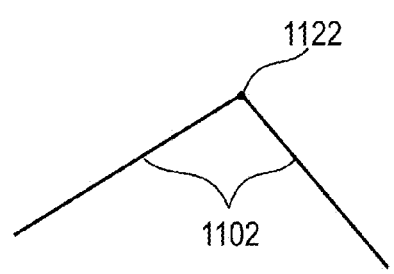
FIGS. 11A-11C schematically illustrate exemplary end portions of plastically deformable fibers with welded ends, in accordance with some embodiments of the present invention.
Figure 11B:
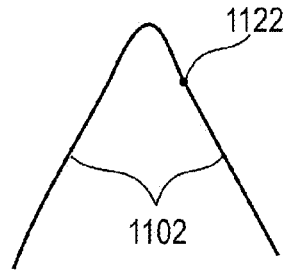
Figure 11C:
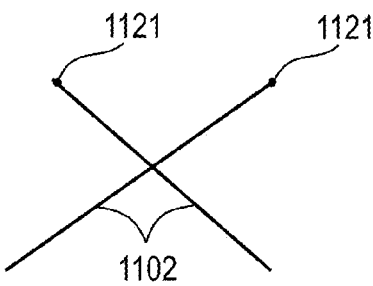
Figure 11D:
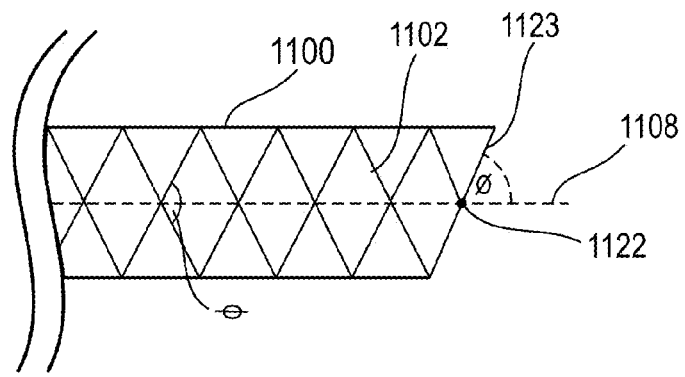
FIG. 11D schematically illustrates an exemplary support with the end portions of the fibers shown in FIG. 11A-11C welded in a connection, in accordance with some embodiments of the present invention.

In some embodiments of the present invention, in addition to, or as an alternative to, using a cover and/or a sleeve as previously described for support 1000 shown in FIG. 10A-10C, the end portions of plastically deformable fibers 1102 may be subject to a heat treatment and/or soldering, which may include laser heating. The heat treatment may be used, as seen in FIGS. 11A and 11B, for welding together in a single connection 1122 the ends of two, or optionally more, fibers 1122 so that the ends are not exposed, and thereby reducing a risk of injury to a body organ or a vessel due to pricking or piercing. Optionally, the tip of each fiber 1122 may be shaped into a rounded and/or blunted shaped as shown at 1121 in FIG. 11C.

In some embodiments of the present invention, the end portions of fibers 1122 may be welded together to form an end portion in support 1100 including an opening 1123 forming an angle ø with axis 1108. The end portion with angled opening 1123 may be fitted over an anastomosed area as shown further on below in FIG. 13C. The angle ø may range from 20-80 degrees relative to axis 1108, for example from 20-40 degrees, from 20-55 degrees, from 20-65 degrees, and may optionally be 60 degrees.

Figure 12A:
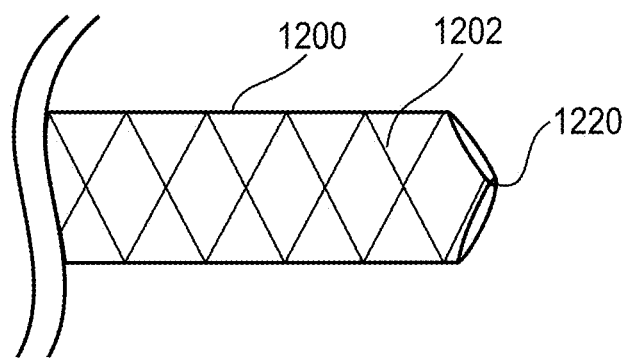
FIGS. 12A and 12B schematically illustrate exemplary end portions of a plurality of plastically deformable fibers looped together at a looping point and forming an end to a vein support, in accordance with an embodiment of the present invention.
Figure 12B:
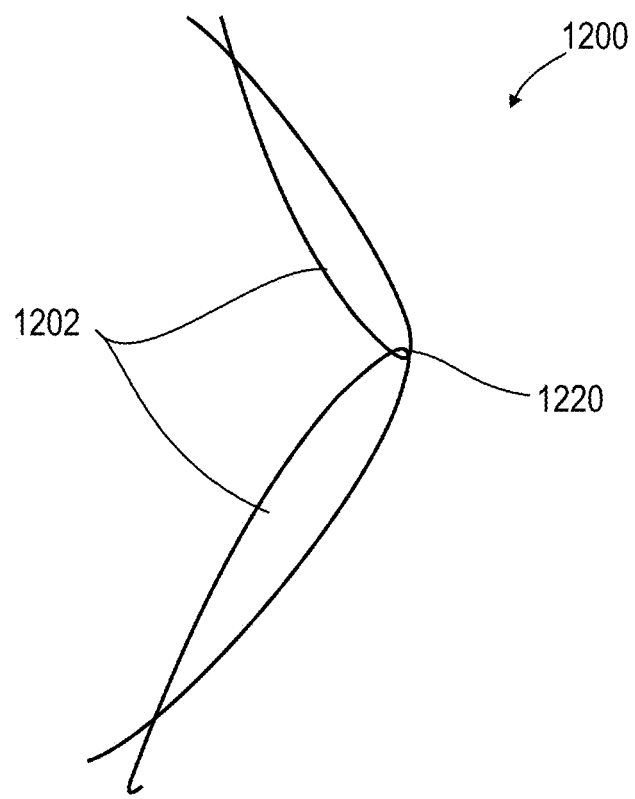

Reference is made to FIGS. 12A and 12B which schematically illustrate exemplary end portions of a plurality of plastically deformable fibers 1202 looped together at a looping point 1220 and forming an end to a vein support 1200, in accordance with an embodiment of the present invention. Looping the end points of fibers 1202, which may include two or more fibers, may substantially prevent the ends from being exposed, and may as a result reduce a risk of injury to a body organ or a vessel due to pricking or piercing. Vein support 1200 may be the same as vein support 100 shown in FIG. 1. Optionally, vein support 1200 may be the same as that shown in FIG. 2, 3, 4, 5A, 7A, 8A, or 9B at 200, 300, 400, 500, 700, 800 or 900, respectively.

In some embodiments of the present invention, the ends of looped fibers 1202 may be attached to support 1200 by welding or some other means which may include any of those previously described, or any combination thereof, so as to prevent their protruding from the end portion. Optionally, plastic deformable fiber 1202 is looped around at the end portion of support 1200 and is used to form a second plastic deformable fiber. Additionally or alternatively, fiber 1202 is repeatedly looped around at the ends of support 1200 to form a plurality of plastically deformable fibers.

Figure 13A:
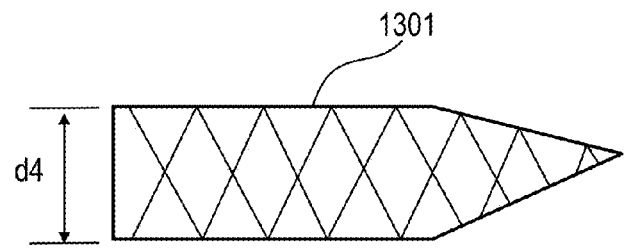
FIGS. 13A-13C schematically illustrate an insert for attaching a vein support to an anastomosis on a body organ, in accordance with an embodiment of the present invention.
Figure 13B:
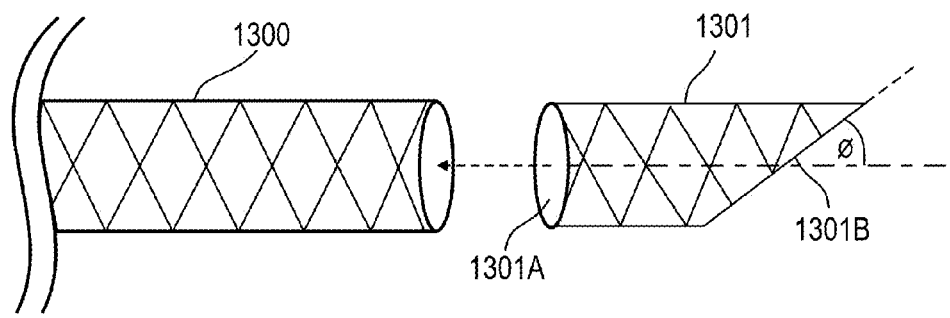
Figure 13C:
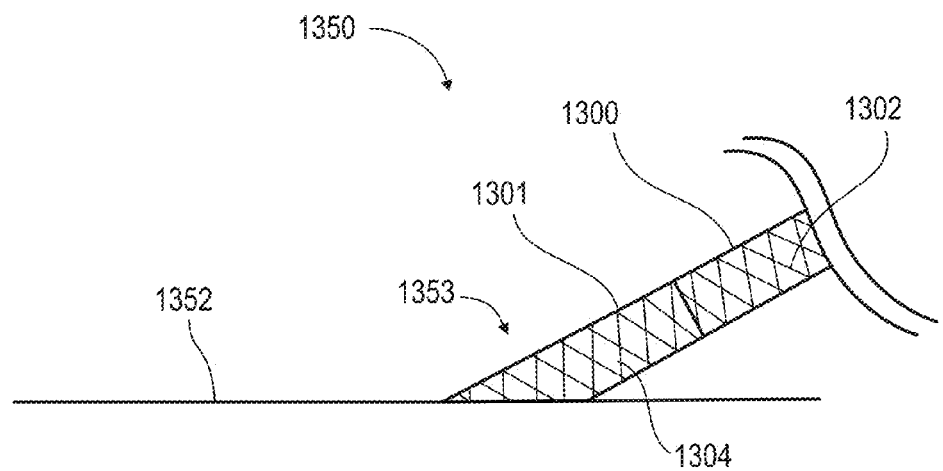

Reference is made to FIGS. 13A-13C which schematically illustrate an extension 1301 for attaching a vein support 1300 including a graft vessel 1353, optionally mounted on the graft optionally sleeved thereon, to a side of a body organ 1352, in accordance with an embodiment of the present invention. Vein support 1300 may be the same as vein support 100 shown in FIG. 1. Optionally, vein support 1300 may be the same as that shown in FIG. 2, 3, 4, 5A, 7A, 8A, or 9B at 200, 300, 400, 500, 700, 800 or 900, respectively.

Occasionally, an end portion of graft vessel 1353 is angled so as to allow for the connection of the graft to a side portion of a target vessel, for example body organ 1352, Additionally, in some circumstances, a second end of the graft is may also be angled for connection to a second vessel which is not parallel to the target vessel. If support 1300 does not include an angled opening, for example angled opening 1123 as previously shown in FIG. 11D, an operator may encounter difficulties covering the angled end portion of the graft with a corresponding end portion of the support.

In some embodiments of the present invention, extension 1301 is added to support 1300 as an elastic end portion specifically designed to fit over anastomosis area. Extension 1301 is optionally connected to an end portion of support 1300 only after the latter has been mounted and/or stretched and/or shaped to fit a target vessel. Extension 1301 may be made from a flat mesh including elastic fibers 1304 as shown in FIG. 13A which is cut at one end so that, when the mesh is rolled to form the extension, on angled opening 1301B includes the angle ø relative to an axis 1308 of the support. The angle ø may range from 20-80 degrees relative to axis 1308, for example from 20-40 degrees, from 20-55 degrees, from 20-65 degrees, and may optionally be 60 degrees. Optionally, extension 1301 may include plastically deformable fibers which may be the same as fibers 102 in support 100.

Figure 14A:
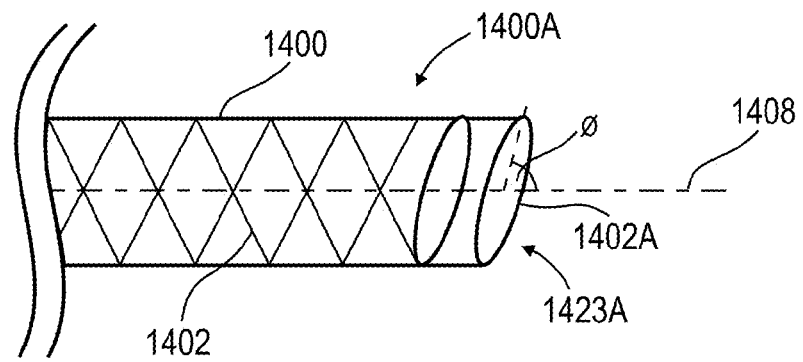
FIGS. 14A-14C schematically illustrate exemplary end portions a vein support for attaching over a distal anastomosis and over a proximal anastomosis, respectively, in accordance with some embodiments of the present invention.
Figure 14B:
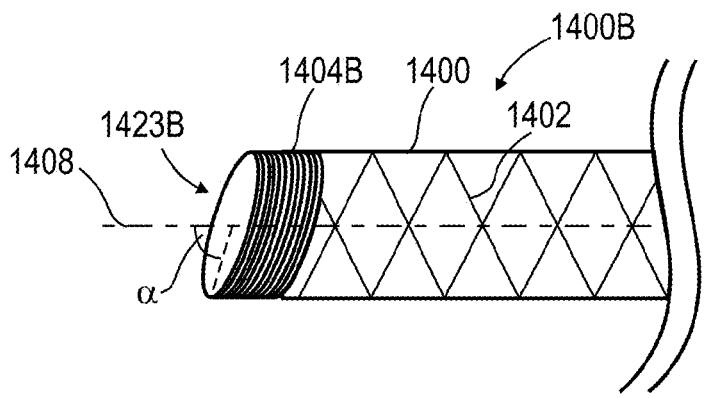
Figure 14C:
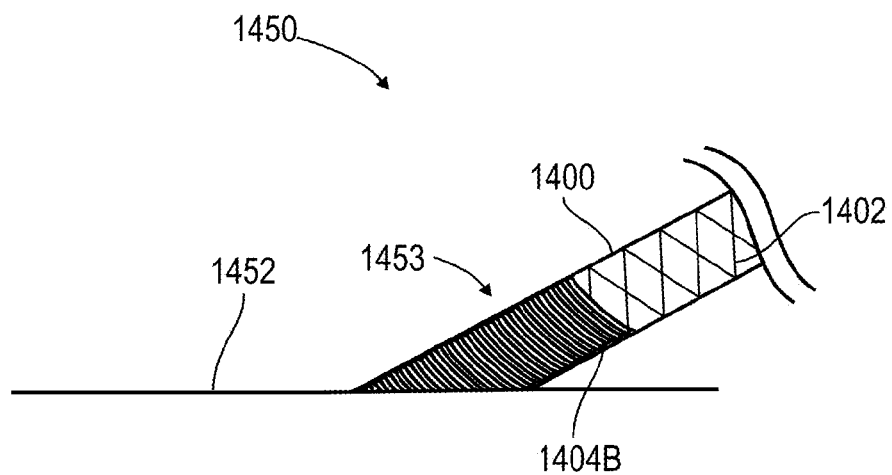

In some embodiments of the present invention, the mesh may be cut on an opposing end to that which will be used to form the angled opening, to a width d4 for forming a second opening 1301A when the mesh is rolled. The width d4 may be such that extension 1301 may be accommodated a certain distance inside a lumen 1306 of support 1300, for example d4 may be between 4 to 6 mm Reference is made to FIGS. 14A-14C which schematically illustrate exemplary end portions 1400A and 1400B of a vein support 1400 for attaching angled ends of a graft vessel 1453 to a distal vessel (FIG. 14A) and to a proximal vessel (FIGS. 14B and 14C), respectively, in accordance with some embodiments of the present invention. Vein support 1400 may be the same as vein support 100 shown in FIG. 1. Optionally, vein support 1400 may be the same as that shown in FIG. 2, 3, 4, 5A, 7A, 8A, or 9B at 200, 300, 400, 500, 700, 800 or 900, respectively.

End portion 1400A may include one or more circular loops 1402A formed from one or more plastically deformable fibers 1402 the circular loops formed by welding or some other means which may include any of those previously described, or any combination thereof, so as to prevent their protruding from the end portion. Circular loops 1402A may be optionally formed so that end portion 1400A includes an opening 1423A, which includes an angle, for example angle ø relative to an axis 1408 of support 1400, for attaching graft vessel 1453 to the side of the distal vessel (not shown). The angle ø may range from 20-80 degrees relative to axis 1408, for example from 20-40 degrees, from 20-55 degrees, from 20-65 degrees, and may optionally be 60 degrees. Circular loops 1402A may be optionally covered by elastic fibers such as for example fiber 1404A so as to prevent possible causing of injury to the target vessel due to protruding ends from fibers 1402.

End portion 1400B may include a plurality of non-plastic deformable fibers configured to form an angular flexible connector 1404B including an opening 1423B which includes an angle, for example angle α relative to axis 1408 of support 1400, for attaching graft vessel 1453 to the side of proximal vessel. 1452. Angle α may range from 20-160 degrees relative to axis 1408, for example from 20-60 degrees, from 60-90 degrees, from 90-120 degrees, from 120-150 degrees, and may optionally be 150 degrees.

Exemplary "Spine"-Type External Support

Figure 15A:
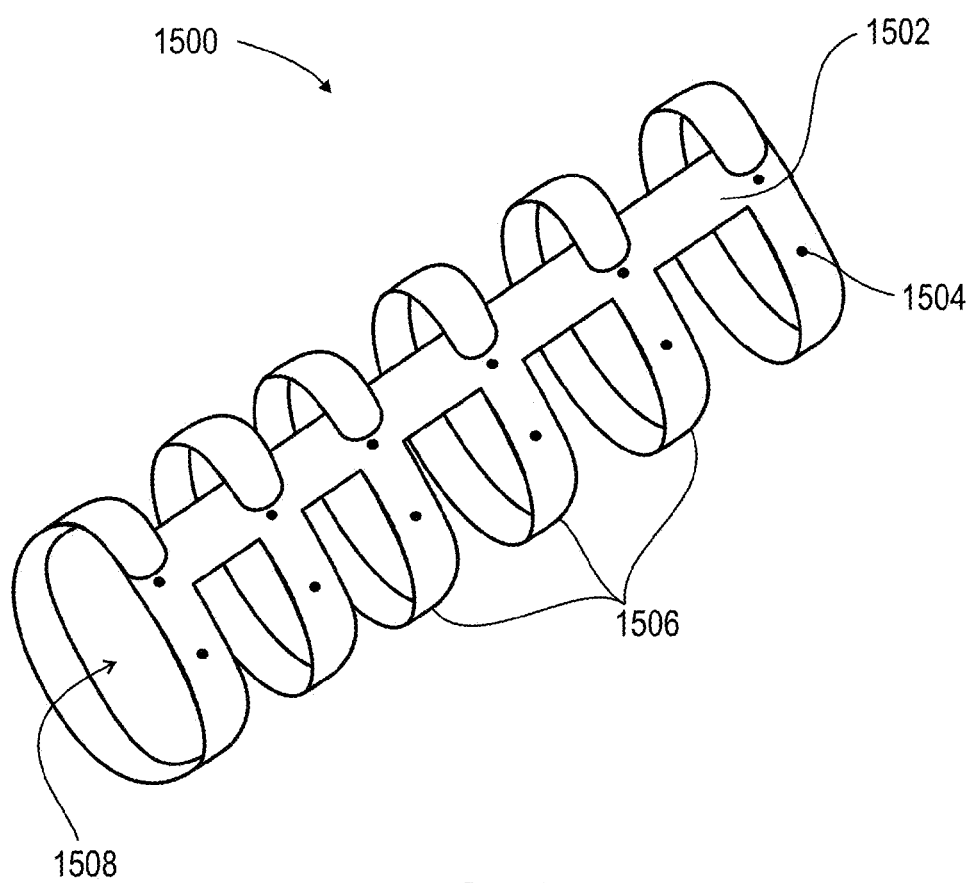
FIG. 15A schematically illustrates an exemplary graft casting support in accordance with an embodiment of the present invention.

Reference is made to FIG. 15A which schematically illustrates an exemplary graft casting support 1500 in accordance with an embodiment of the present invention. Support 1500 comprises a spine portion 1502 from which extend a plurality of rounded fasteners 1506 defining a lumen 1508 for securing the graft inside. A length of support 1500 may be selected to be slightly less than a length of a grafted artery, and a diameter of the lumen 6 may be selected to accommodate the grafted artery inside. Fasteners 1506 may be made from a resiliently flexible or plastically deformable material, while spine 1502 may be made from a plastically deformable material which enables an operator to bend and/or twist the support. Each fastener 1506 may be opened to admit a portion of the grafted artery into lumen 1508, as described further on below. If fastener 1506 is elastic, after inserting a portion of a vein or arterial graft into lumen 1508, the fastener will elastically recover its rounded shape securing the graft. If fastener 1506 is plastically deformable, the fastener may be deformed manually into the rounded shape securing the graft.

Figure 15B:
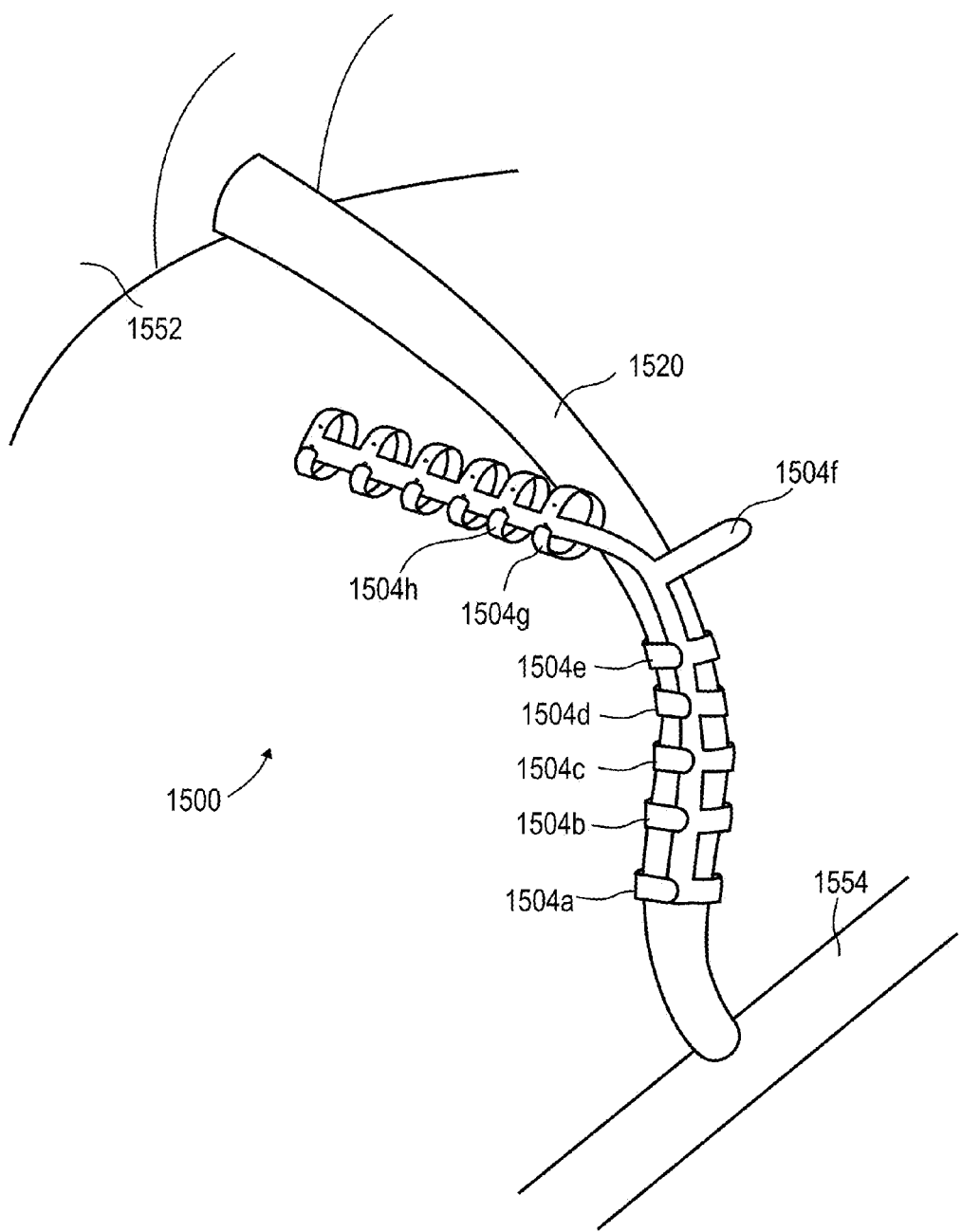
FIG. 15B schematically illustrates a portion of a heart to which a coronary artery is grafted, and a method to support the artery with a support, in accordance with some embodiments of the present invention.

Reference is made to FIG. 15B which schematically illustrates a portion of a heart 1552 to which a coronary artery 1520 has been grafted, and a method to support the artery with support 1500, in accordance with some embodiments of the present invention. Optionally, before, during or after performing an anastomosis to the aorta or coronary artery, the vein graft or arterial graft 1520 may be inserted into lumen 1508 of support 1500.

Shown in the figure is a segment of graft 1520 which has been inserted into lumen 1508 defined by first five fasteners 1504a to 1504e. A next step in the process is to insert an additional segment of graft 1520 into lumen 1508 of fastener 1504*f*. Fastener 15044*f* is first straightened, as shown in the figure, and is then tucked under artery 1520. Optionally, due to a resiliently flexible nature of fastener 1504, after being tucked under graft 1520, fastener 4*f* elastically, optionally with assistance from the operator, regains its rounded shape securing the graft. This process is then repeated with each subsequent fastener 1504*g*, 1504*h*, and so on, until all fasteners 1504 secure graft 1520.

In some embodiments of the present invention, spine 1502 may be made from a material with sufficient plastic deformability to allow the operator to fixedly deform the support, and hence the arterial or vein graft 1520 secured by the support, into a desired shape. Optionally, the material of support 1500 may be further selected so as to withstand deformation forces applied to it by adjacent anatomical structures or surgical materials. Thus, the supported arterial or vein graft is protected by support 1500 from kinking and/or collapsing and/or deviating direction, allowing a patency and a desired path of the graft to be maintained. Optionally, spine 1502 and/or fasteners 1504 may be made, for example, from stainless steel or other metals, some plastic derivatives, Teflon®, reinforced Dacron® or other suitable materials. Support 1500 may be optionally made from a biodegradable material such as vicril or other suitable materials, to allow the sleeve to be absorbed after a predetermined period of time, such as a few weeks, after the scar tissue has stabilized. Spine 1502 and/or the fasteners 1504 may elute a pharmacological substance, such as vasodilators (such as slow releasing nitroglycerin or a nitric oxide (NO) releasing substances), anti-platelet agents (such as aspirin, clopidogrel) immunosuppressant drugs (such as tacrolimus, sirolimus), an anticoagulant drug (such as heparin, low molecular heparins, hirudin derivatives) for prevention of blood clotting, in order to reduce graft thrombosis and improvement of the graft or vessel patency, and any other pharmacologic substance. Support 1500 and/or fasteners 1504 may include radio-opaque markers so as to allow it to be observed by imaging procedures such as radiography, CT, or angiography, without a need for contrast material. This may facilitate monitoring of the graft after surgery and planning of a re-operation without a need for cardiac gated multi detector CT or the use of contrast material, and protection of the graft while performing a "re-do" cardiac or thoracic procedure. Radio-opaque markers may also facilitate engagement of the graft by a catheter during coronary angiography.

Figure 16A:
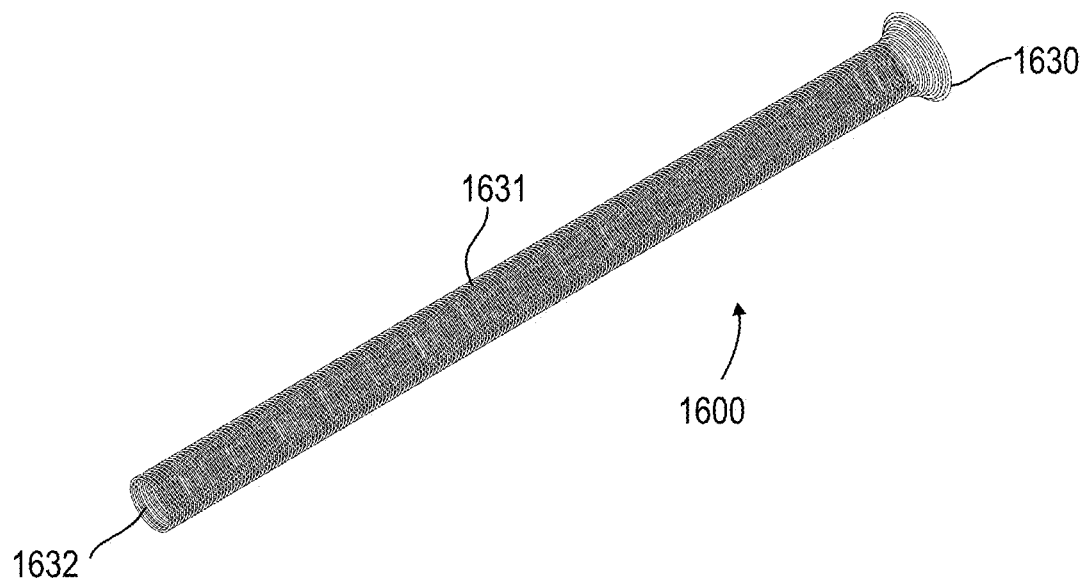
FIGS. 16A and 16B schematically illustrate a graft casting support, in accordance with some embodiments of the present invention.
Figure 16B:
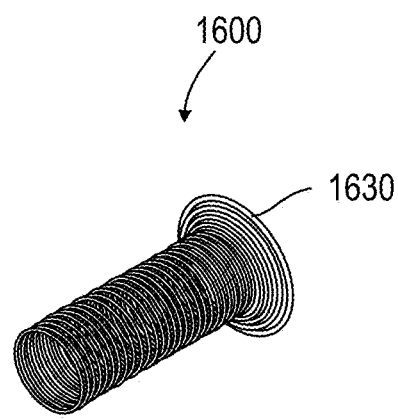

Reference is made to FIGS. 16A and 16B which schematically illustrate a graft casting support 1600, in accordance with some embodiments of the present invention. Support 1600 comprises a cylindrical shaft portion 1631 having a lumen 1632 formed by a coiled or braided wire. Shaft portion 1631 may be plastically deformable so as to allow an operator to provide it with a shape in which it remains in a body. One or both ends of shaft portion 1631 may include a conical termination 1630 which is shown enlarged in FIG. 16B. Conical termination 1630 may be left freely or substantially unsecured preferably over the anastomosis, or may serve for attachment of an end of support 1600 to a tissue surface to which and en of the grafted artery may be attached. Attachment of conical termination 1630 may be by gluing, hooking or sewing the conical termination to the tissue surface. The length of support 1600 may be selected to be the same as, or slightly less than, a length of the graft, while a diameter of lumen 1632 is selected to accommodate a vein or an arterial graft. The length of support 1600 may be cut to a desired length prior to, during, or optionally after deployment. Alternatively, support 1600 may be stretchable to a desired length and attached at the ends to maintain the desired length. This avoids a need to cut the support during insertion. When stretchable, support 1600 may accommodate a range of lengths, so that a set of supports wherein each support accommodates a different range of lengths may accommodate a very broad range of lengths. Support 1600 may store or elute a pharmacological substance as described previously and may also be partially or fully radio opaque or biodegradable.

EXAMPLES

Reference is now made to the following examples, which together with the above descriptions; illustrate some embodiments of the invention in a non limiting fashion.

TABLE 1

Calculated mechanical properties of an optional example for a support with 38 elastic wires of 0.05 mm in diameter, braided on 8 mm mandrel and using 150° braiding angle

| Device Diameter [mm] | Braid Angle [deg] | Device Length [mm] | Axial Stiffness [N/m] |
|---|---|---|---|
| 8.00 | 140.68 | 78.00 | 0.59 |
| 7.50 | 123.79 | 109.21 | 0.75 |
| 7.00 | 110.67 | 131.86 | 0.96 |
| 6.50 | 99.43 | 149.89 | 1.23 |
| 6.00 | 89.38 | 164.81 | 1.61 |
| 5.50 | 80.13 | 177.42 | 2.14 |
| 5.00 | 71.47 | 188.18 | 2.91 |
| 4.50 | 63.26 | 197.39 | 4.07 |
| 4.00 | 55.39 | 205.26 | 5.91 |
| 3.50 | 47.80 | 211.94 | 8.98 |
| 3.00 | 40.43 | 217.54 | 14.56 |

Exemplary Shapeable External Vein Support and Method of Production Thereof

Figure 17A:
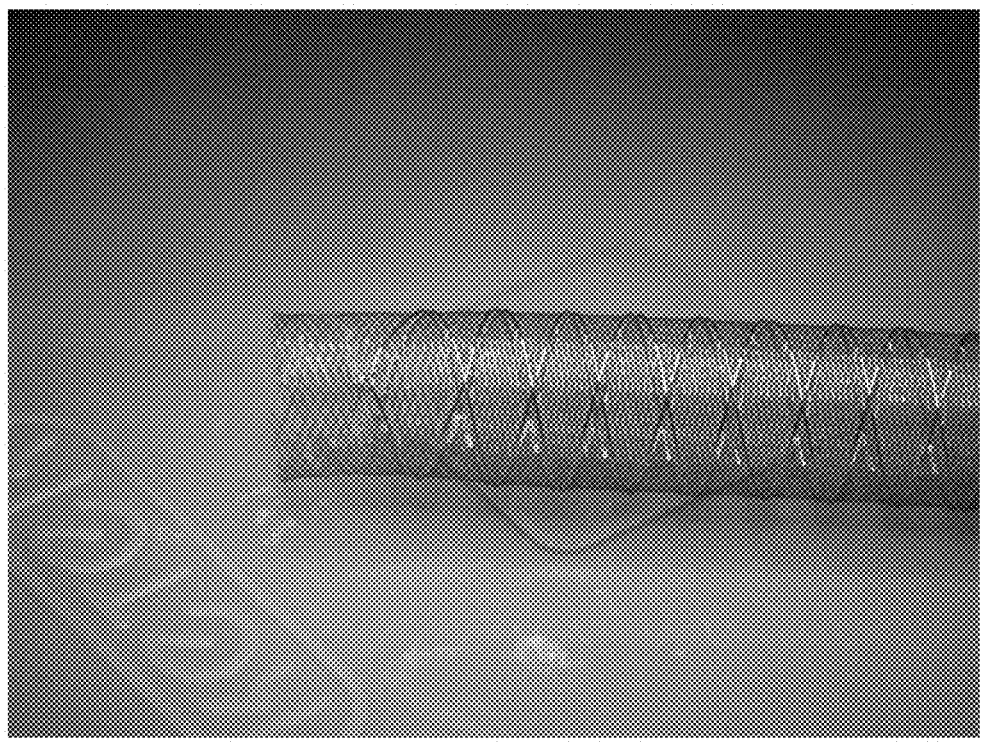
FIGS. 17A and 17B depict photographs of a portion of an extended support substantially resembling that used in a CABG procedure, and an enlarged view of a section of the support, respectively, in accordance with some embodiments of the present invention.
Figure 17B:
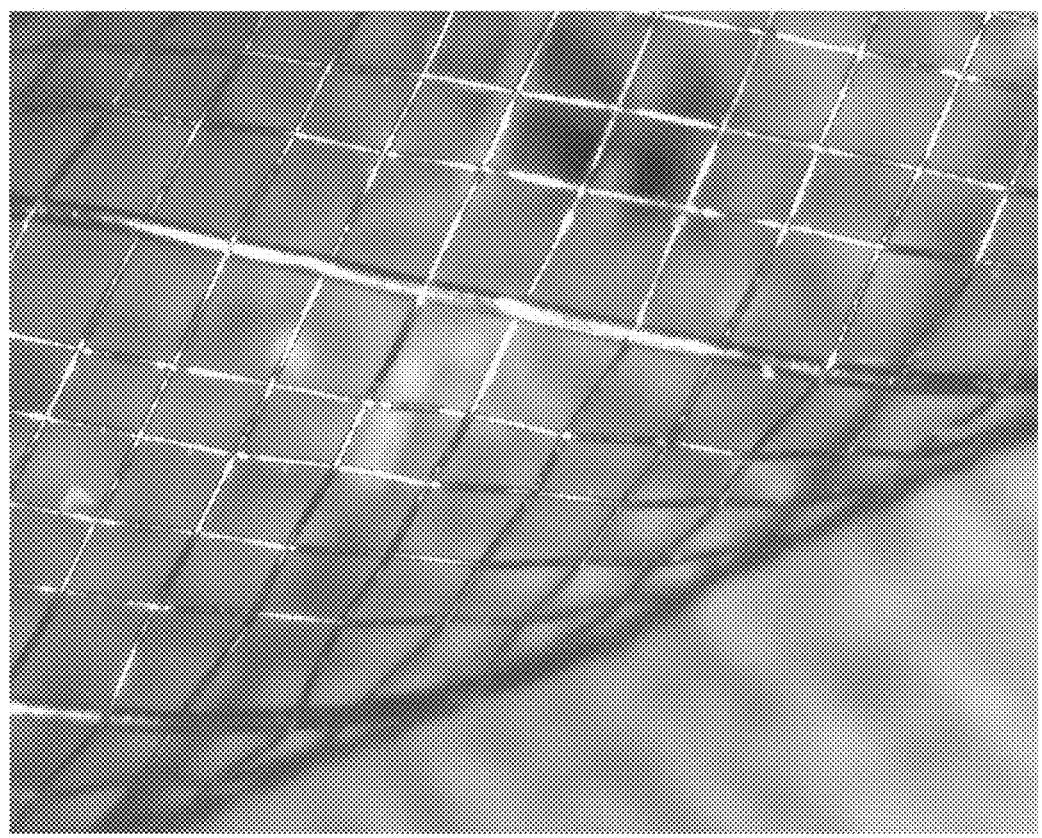

Photographs have been included as FIG. 17A and FIG. 17B depicting a portion of an exemplary extended support and an enlarged view of a section of support, respectively, in accordance with some embodiments of the present invention.

The support includes 42 cobalt chrome wires in a braided tubular configuration affording radial elasticity and axial plasticity, comprising 38 elastically deformable wires of a first type (43 microns diameter each) and 4 annealed plastically deformable wires of a second type (150 microns diameter each), the wires intertwined symmetrically in the braid.

The support may be supplied compressed in various lengths and internal diameters in order to provide more flexibility to the surgeon in addressing different situations. The inner diameter of the device, in its compressed form, is chosen so as to allow a substantially comfortable overlaying the device over the bypass graft after completion of distal anastomosis.

Accordingly, the support may be manufactured in optionally 4 initial configurations, each having a different range of inner diameters pre- and post-extension:

8 mm (compressed)→5 mm (extended to the desired length), 7 mm (compressed)→4 mm (extended to the desired length), and 6 mm (compressed)→3 mm (extended to the desired length).

The support may be additionally manufactured in 6-8 different final lengths ranging from 2 cm-35 cm (post-extension) to allow adequate matching between the support and the vein graft along its length.

The support is optionally configured as substantially kink-resistant and axially symmetric in 0 to 180 degrees of bending. In a compressed form, the support shows relative radial plasticity and axial elasticity, whereas when extended, it possesses relative axial plasticity (low springback) and radial elasticity (crush resistance) throughout its length.

The support braiding can be performed using a 42 carrier braiding machine on a 304/316 SS mandrel cleaned with isopropyl alcohol. The mandrel diameter may be for example 8, 7, or 6 mm depending on the extended (maximally-allowed stretched) length of the support. The braiding angle may be approximately 150 degrees.

In order to prevent damage to the heart/vascular tissue, the annealed wires may be looped (on each other) and welded with laser at a distance of approximately 5 mm from the proximal end of the support. An annealed distal end of the support may end in a 30-to-60 angle, the annealed wires looped and welded at a distance of approximately mm from the end, which enables the surgeon to match it and cover the distal anastomosis.

Several weeks after implantation, fibrotic tissue grows into the device, covering and affixing the vein graft and the support together. Accordingly, the annealed wires may be at least partially radio opaque to enable imagery during a Percutaneous Coronary Intervention (PCI).

Following implantation, the resulting graft-support has a limited radial elasticity with substantially resilient properties so that, if the support is crushed, it returns to its substantially pre-crushed diameter allowing the graft to also return to its normal diameter. Furthermore, the radial compliance is substantially small so that the radial movements (such as in pulse movements) are much smaller compared to that of natural arteries. For example, the radial compliance in supports similar to that shown in FIG. 17A, or for variations of that shown in the figure, the variation being in the number of wires, types of wires, or diameter of wires, or any combination thereof, is typically in one of the ranges of 0-10%/mm Hg; 0-5%/mm Hg; less than 3%/mm Hg (together with the vein graft). In some variations, the radial compliance may also be in the range similar to that of a native artery, for example, 3-30%/mm Hg (but will display other properties than that of the native artery due to the vein support).

Exemplary CABG Procedure Incorporating Exemplary Shapeable Vein Support

Reference is made to FIGS. 18A-18F which schematically illustrate a typical implantation procedure of the support shown in FIG. 17A, as may be followed by a surgeon performing a CABG procedure, in accordance with some embodiments of the present invention.

Figure 18A:
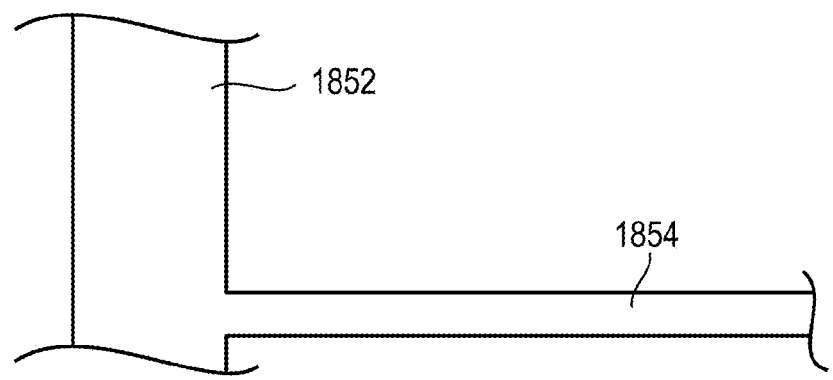
FIGS. 18A-18F schematically illustrate a typical support implantation procedure as followed by a surgeon performing a CABG procedure, in accordance with some embodiments of the present invention.

Shown in FIG. 18A is a schematic illustration of the aorta 1852 and a coronary artery 1854 which is to be bypassed by a graft. After harvesting the vein grafts, and clamping the collaterals on the grafts, the surgeon measures their length and diameter.

Figure 18B:
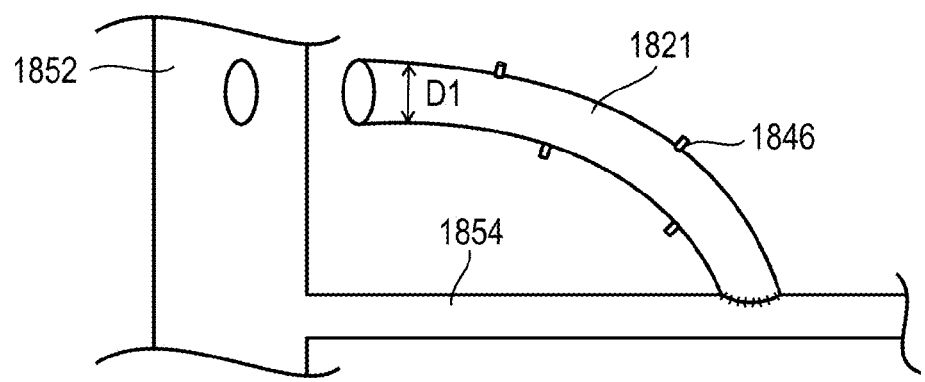

Only after performing a $1^{st}$ anastomosis, the surgeon has a final reliable judgment regarding the length of the graft. FIG. 18B schematically illustrates a graft 1821 attached at a distal end to artery 1854 in the $1^{st}$ anastomosis. Graft 1821 is shown with a plurality of collaterals 1846, and has a reduced diameter D1 as there is no blood flow through the graft.

Figure 18C:
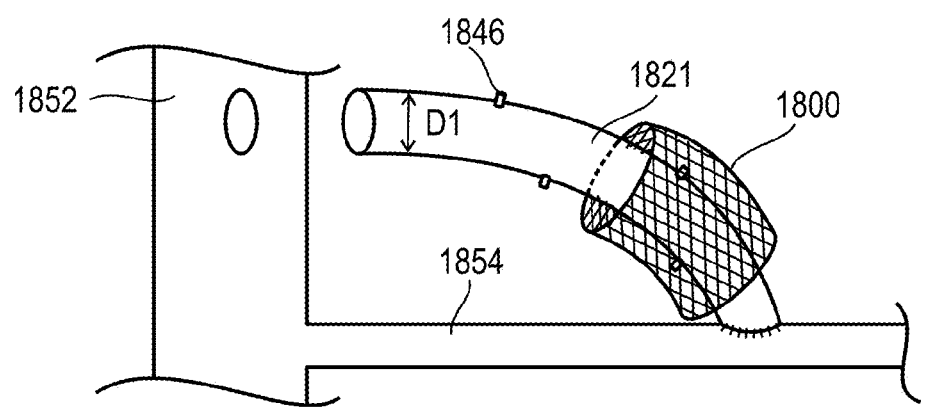

FIGS. 18B and 18C schematically illustrate the next phase of the support implantation procedure following described. After choosing a $2^{nd}$ anastomosis site on aorta 1852, the surgeon measures the exact length and/or diameter(s) of graft 1821 and chooses the right support 1800. Optionally, the surgeon can choose the right support from a support implantation table, such as the following exemplary table:

| Bypass graft outer diameter | 3 mm | 4 mm | 5 mm | 6 mm |
| --- | --- | --- | --- | --- |
| A | 10.7 cm | 10.0 cm | 9.2 cm | 8.0 cm |
| B | 13.3 cm | 12.5 cm | 11.4 cm | 9.8 cm |
| C | 16.2 cm | 15.0 cm | 13.8 cm | 11.9 cm |
| D | 18.8 cm | 17.5 cm | 16.0 cm | 13.8 cm |
| E | 21.2 cm | 20.0 cm | 18.1 cm | 15.7 cm |
| F | 24.0 cm | 22.5 cm | 20.6 cm | 17.8 cm |

The surgeon may then gently thread support 1800 over graft 1821 and completes the $2^{nd}$ anastomosis.

Figure 18D:
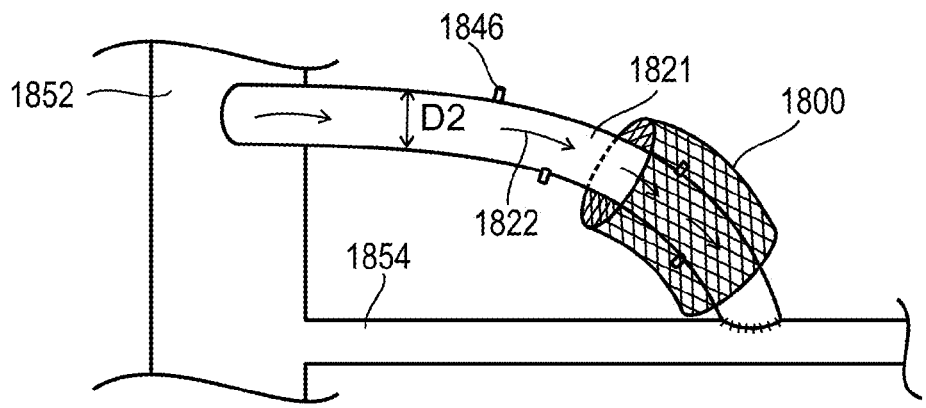
Figure 18E:
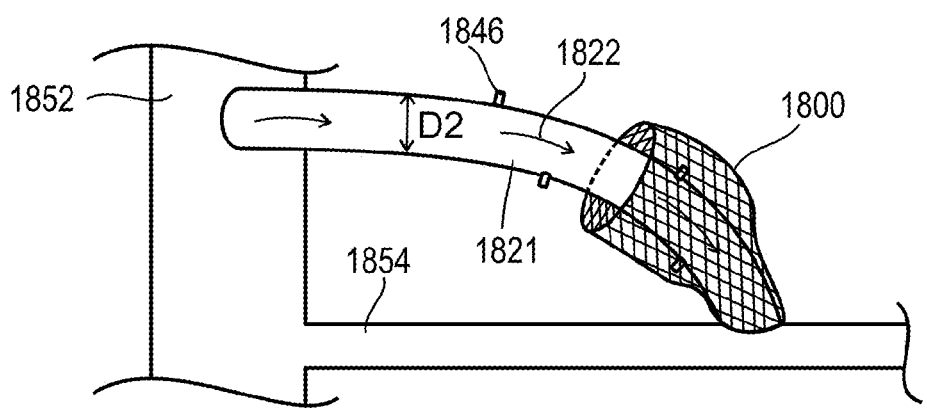

FIGS. 18D and 18E schematically illustrate the next phase of the support implantation procedure following described. Following recovery of blood flow 1822 in graft 1821 and after assessing the vein graft flow and checking it for leaks at collaterals 1846 and at the anastomosis site, the surgeon opens support 1800 to the desired length while he fully controls the opening of the support with its wide part in a distal section (in order to avoid damage to the clips on the collaterals). The diameter of graft 1821 increases from diameter D1 to a new diameter D2 as a result of blood flow 1822 in the graft, diameter D2 is substantially greater than, optionally about three times, D1.

Figure 18F:
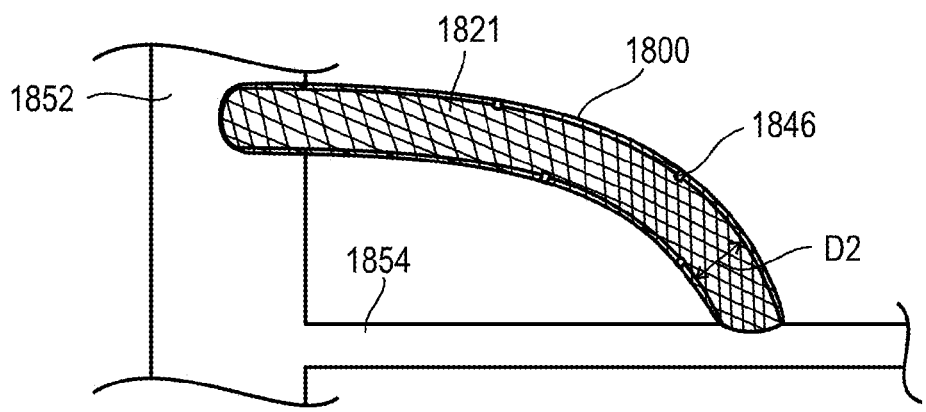

FIG. 18F schematically illustrates the last phase of the procedure. The surgeon gently covers the proximal and distal anastomosis and shapes support 1800 and support-covered graft 1821 according to the desired path in the chest from artery 1854 to aorta 1852. At the end of the procedure, support 1800 covers relatively tightly substantially the whole length of graft 1821, including collaterals 1846. Support 1800 maintains its shape, length and diameter, and enables the surgeon to safely terminate the procedure.

Tests and Observations

Reference is now made to the following tests and observations, which together with the above descriptions; illustrate some embodiments of the invention in a non-limiting fashion.

The inventors conducted a feasibility study including a CABG procedure on a sheep to evaluate the formable tubular support's positioning procedure; to evaluate safety of the support; and to evaluate the support's initial performance. The sheep was selected as its cardiovascular system is similar to that of humans; the sheep's growth rate is low comparing to other applicable models (e.g. swine model), allowing for a relatively long follow up period without substantial change in the size of organs; and the vein harvesting procedure is relatively easier and efficient compared to other applicable models. The support, which is substantially similar to the support shown in FIG. 17A, was placed over a vessel as part of the CABG procedure.

For the CABG procedure a domestic sheep, female, aged 12 months, weight 76 kg was used. The sheep was handled according to the international guidelines for care and use of laboratory animals, with food and water made available regularly on a daily basis, and the room where the sheep was kept cleaned daily using a commercial disinfecting detergent.

The CABG operation performed was an off pump procedure. In the operation, the saphenous veins were harvested from both legs and two bypass grafts were constructed. The sheep's arteries to which the vein grafts were anastomosed were the left anterior descending (LAD) artery and the circumflex artery ($1^{st}$ marginal). The experimental graft, with the external support, was the bypass vein graft to the LAD. The control graft was bypassed to the marginal artery. After the completion of the experimental graft's first anastomosis, the surgeon measured again the graft's length and diameter and chose the right external support (the length of the experimental graft was 15 cm and its diameter was 6.5 mm), optionally from a support implantation table. The length of the control graft was 12 cm and its average diameter was 6.7 mm). Afterwards, the external support, in its compressed form, was threaded over the graft and the second anastomosis was performed. After assessing both grafts flow and after completing the final checkup of the vein grafts, their collaterals, and the anastomosis site, both native arteries were ligated proximally to the distal anastomosis site.

After recovery of blood flow into the graft, the surgeon opened the support to the desired length and shaped its path within the chest. The support was opened to a length which covered entirely and gently the anastomosis site. At the end of the procedure, after closing the chest, the sheep underwent angiography which demonstrated that both grafts were open with good flow.

At the end of a follow up period of 3 months, the sheep underwent a second coronary angiography to assess the graft's patency and its intimal and medial hyperplasia rates (lumen's internal diameter and inner walls contour). The experimental graft was seen to be entirely open, with excellent laminar flow. The vein graft internal diameter was the same as in the implantation day and its internal walls were uniform.

Following angiography, the animal was sacrificed and the grafts and the heart were harvested. The grafts and heart were washed with 0.9% NaCl and immersed in 4% formaldehyde for 24 hours. Macroscopically, no damage to the heart was viewed and the graft and support, similarly to the rest of the operational field, was embedded in connective tissue and fat. The external support was fixed to the vein graft and was located where it was positioned at the end of the surgery, and was of the same length and diameter.

Exemplary In-Vitro Testing of an Exemplary Shapeable Vein Support

An In vitro testing for long axis stability was conducted to collect data regarding the length/diameter stability of the support and its capability to maintain a desired shape after being deployed in high pressure/high pulse physiological conditions resembling that of the human body. Physiological conditions simulated included those associated with body temperature control (37° C.), pressure control (systolic and diastolic pressure) and pulse control. The experimental setup consisted of plastic tubes simulating arteries/veins in which fluid flows (distilled water simulating blood) in a closed loop by using a peristaltic pump simulating the heart. The entire system data and parameters monitored were controlled and collected by data acquisition software. Use of a high quality PC camera in real time during the testing allowed an accurate measurement of support length/diameter at any given time.

The long axis stability of the support system was tested according to the following table:

| Device Code | Pulse | Systolic pressure (mmHg) | Temp. (Celsius) inside the vessel | Temp. (Celsius) inside the bath | Experiment time (minutes) |
|---|---|---|---|---|---|
| | 120 | 120 | 36-38 | 36-38 | 10 |
| | 120 | 220 | 36-38 | 36-38 | 10 |

-continued

| Device Code | Pulse | Systolic pressure (mmHg) | Temp. (Celsius) inside the vessel | Temp. (Celsius) inside the bath | Experiment time (minutes) |
|---|---|---|---|---|---|
| | 120 | 120 | 36-38 | 36-38 | 60 |
| | 120 | 220 | 36-38 | 36-38 | 60 |

Two different supports were tested, a first support comprising 38 cobalt chrome elastically deformable wires (50 microns diameter each) and 4 annealed plastically deformable cobalt chrome wires (150 microns diameter each); and a second support comprising 36 cobalt chrome elastically deformable wires (50 microns diameter each) and 6 annealed plastically deformable cobalt chrome wires (150 microns diameter each). The result of the in vitro tests showed no difference between the initial and final length of each support; that the supports can maintain their length/diameter and shape in relatively extreme physiological conditions; and that 4 annealed plastically deformable cobalt chrome wires may be used in lieu of 6 annealed plastically deformable cobalt chrome wires. Based on the results of the in vitro testing, the inventors have additionally determined that other suitable braided configurations for the support with higher radial compliance (as previously stated), may include a braid comprising 40 elastically deformable cobalt chrome wires of diameter 43 microns and 2 annealed plastically deformable cobalt chrome wires of diameter 150 microns, and a braid with the same number of wires as the first braid tested but with 4 annealed plastically deformable cobalt chrome wires of diameter 100-125 microns.

GENERAL COMMENTS

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find analytical support in the following examples.

What is claimed is:

1. A method of supporting a vein, the method comprising:
   mounting a vein support around the vein; and
   plastically deforming said vein support relative to a longitudinal axis of said vein support, while said vein support is mounted on the vein, such that following said plastically deforming, said vein support substantially maintains a new shape relative to said axis;
   wherein said plastically deforming said vein support includes plastically bending said vein support in a direction transversally to said axis.

2. The method of claim 1, wherein said plastically deforming said vein support includes plastically stretching said vein support along said axis.

3. The method of claim 1, wherein said plastically deforming is performed by manipulating said vein support sufficiently to impose a plastic deformation of said vein support that alters a length of said vein support from a pre-deformation relaxed length to a post-deformation relaxed length different than said pre-deformation relaxed length.

4. The method of claim 3, wherein length of said vein support is coupled to a cross-sectional diameter of said vein support so that said plastic deformation alters said diameter from a pre-deformation relaxed diameter to a post-deformation relaxed diameter different than said pre-deformation relaxed diameter, and wherein said post-deformation diameter is selected in response to a diameter of the vein.

5. The method of claim 1, wherein said plastically deforming defines a layout of the vein independent of any attachment of said vein support to tissue other than the vein.

6. A method of supporting a vein, the method comprising:
   mounting a vein support around the vein; and
   deforming said vein support, while said vein support is mounted on the vein, sufficiently to impose thereupon a plastic deformation that alters a length of said vein support, from a pre-deformation relaxed length to a post-deformation relaxed length different than said pre-deformation relaxed length.

7. The method of claim 6, wherein length of said vein support is coupled to a cross-sectional diameter of said vein support so that said deforming alters said diameter from a pre-deformation relaxed diameter to a post-deformation relaxed diameter different than said pre-deformation relaxed diameter, and wherein said post-deformation diameter is selected in response to a diameter of the vein.

8. The method of claim 6, wherein the vein has a first vein diameter at a first axial location of the vein and a second vein diameter at a second axial location of the vein, wherein said deforming is performed so that said vein support has a first vein support diameter adjacent said first axial location and a second vein support diameter corresponding to said second vein diameter adjacent said second axial location.

9. The method of claim 6, wherein said deforming said vein support includes any combination of: plastically stretching said vein support along a longitudinal axis thereof, plastically bending said vein support in a direction transversally to said longitudinal axis, and plastically reversely compressing said vein support in a direction along said longitudinal axis.

10. The method of claim 6, wherein said deforming defines a layout of the vein independent of any attachment of said vein support to tissue other than the vein.

11. The method of claim 6, wherein said deforming is performed in-situ in an open surgery with or without a heart-lung machine.

12. The method of claim 6, comprising choosing a configuration of said vein support from a variety of vein support configurations, each of said configurations having a different range of inner diameters between said pre-deformation relaxed length and said post-deformation relaxed length.

13. The method of claim 6, wherein said deforming is preceded by allowing blood to flow in the vein to thereby increase vein diameter.

14. The method of claim 6, wherein said deforming includes manually manipulating said vein support.

15. A method of supporting a vein, the method comprising:
mounting a vein support around the vein;
plastically deforming said vein support relative to a longitudinal axis of said vein support, while said vein support is mounted on the vein, such that following said plastically deforming, said vein support substantially maintains a new shape relative to said axis; and
plastically deforming diameter of said vein support at a plurality of points along a length of said vein support.

16. The method of claim 15, wherein said plastically deforming said vein support includes plastically stretching said vein support along said axis.

17. The method of claim 15, wherein said plastically deforming is performed by manipulating said vein support sufficiently to impose a plastic deformation of said vein support that alters a length of said vein support from a pre-deformation relaxed length to a post-deformation relaxed length different than said pre-deformation relaxed length.

18. The method of claim 17, wherein length of said vein support is coupled to a cross-sectional diameter of said vein support so that said plastic deformation alters said diameter from a pre-deformation relaxed diameter to a post-deformation relaxed diameter different than said pre-deformation relaxed diameter, and wherein said post-deformation diameter is selected in response to a diameter of the vein.

19. The method of claim 15, wherein said plastically deforming defines a layout of the vein independent of any attachment of said vein support to tissue other than the vein.

20. A method of supporting a vein, the method comprising:
mounting a vein support around the vein; and
plastically deforming said vein support relative to a longitudinal axis of said vein support, while said vein support is mounted on the vein, such that following said plastically deforming, said vein support substantially maintains a new shape relative to said axis;
wherein said plastically deforming comprises deforming said vein support along said axis whereby springback of said vein support relative to said axis decreases.

21. The method of claim 20, wherein said plastically deforming said vein support includes plastically stretching said vein support along said axis.

22. The method of claim 20, wherein said springback decreases to a value in a range of 0.5% to 5%.

23. The method of claim 20, wherein said plastically deforming is performed by manipulating said vein support sufficiently to impose a plastic deformation of said vein support that alters a length of said vein support from a pre-deformation relaxed length to a post-deformation relaxed length different than said pre-deformation relaxed length.

24. The method of claim 23, wherein length of said vein support is coupled to a cross-sectional diameter of said vein support so that said plastic deformation alters said diameter from a pre-deformation relaxed diameter to a post-deformation relaxed diameter different than said pre-deformation relaxed diameter, and wherein said post-deformation diameter is selected in response to a diameter of the vein.

25. The method of claim 20, wherein said plastically deforming defines a layout of the vein independent of any attachment of said vein support to tissue other than the vein.

26. A method of supporting a vein, the method comprising:
mounting a vein support around the vein; and
plastically deforming said vein support relative to a longitudinal axis of said vein support, while said vein support is mounted on the vein, such that following said plastically deforming, said vein support substantially maintains a new shape relative to said axis;
wherein said plastically deforming is performed by manipulating said vein support sufficiently to impose a plastic deformation of said vein support that alters a length of said vein support from a pre-deformation relaxed length to a post-deformation relaxed length different than said pre-deformation relaxed length; and
wherein the vein has a first vein diameter at a first axial location of the vein and a second vein diameter at a second axial location of the vein, wherein said manipulating is performed so that said vein support has a first vein support diameter adjacent said first axial location and a second vein support diameter corresponding to said second vein diameter adjacent said second axial location.

27. The method of claim 26, wherein said plastically deforming said vein support includes plastically stretching said vein support along said axis.

28. The method of claim 26, wherein said plastically deforming defines a layout of the vein independent of any attachment of said vein support to tissue other than the vein.

29. A method of supporting a vein, the method comprising:
mounting a vein support around the vein;
plastically deforming said vein support relative to a longitudinal axis of said vein support, while said vein support is mounted on the vein, such that following said plastically deforming, said vein support substantially maintains a new shape relative to said axis; and
connecting a first end of the vein to a first point in a vascular system of a patient with a first anastomosis so as to incorporate the vein into said vascular system.

30. The method of claim 29, wherein said plastically deforming said vein support includes plastically stretching said vein support along said axis.

31. The method of claim 29, wherein said plastically deforming defines a layout of the vein independent of any attachment of said vein support to tissue other than the vein.

32. The method of claim 29, wherein said plastically deforming said vein support is performed after said connecting said first end of the vein to said vascular system.

33. The method of claim 32, additionally comprising connecting a second end of the vein to a second point in said vascular system with a second anastomosis.

34. The method of claim 33, wherein said plastically deforming said vein support is performed after said connecting said second end of the vein to said vascular system.

35. A method of supporting a vein, the method comprising:
mounting a vein support around the vein;
plastically deforming said vein support relative to a longitudinal axis of said vein support, while said vein support is mounted on the vein, such that following said plastically deforming, said vein support substantially maintains a new shape relative to said axis;
attaching the vein to at least two separate points in a vascular system of a patient;
allowing blood to flow in and expand the vein; and
shaping said vein support mounted on the vein during said blood flow.

36. The method of claim 35, wherein said plastically deforming said vein support includes plastically stretching said vein support along said axis.

37. The method of claim 35, wherein said plastically deforming said vein support includes plastically bending said vein support in a direction transversally to said axis.

38. The method of claim 35, comprising plastically deforming diameter of said vein support at a plurality of points along a length of said vein support.

39. The method of claim 35, wherein said plastically deforming comprises deforming said vein support along said axis whereby springback of said vein support relative to said axis decreases.

40. The method of claim 35, wherein said plastically deforming is performed by manipulating said vein support sufficiently to impose a plastic deformation of said vein support that alters a length of said vein support from a pre-deformation relaxed length to a post-deformation relaxed length different than said pre-deformation relaxed length.

41. The method of claim 40, wherein the vein has a first vein diameter at a first axial location of the vein and a second vein diameter at a second axial location of the vein, wherein said manipulating is performed so that said vein support has a first vein support diameter adjacent said first axial location and a second vein support diameter corresponding to said second vein diameter adjacent said second axial location.

42. The method of claim 35, wherein said plastically deforming defines a layout of the vein independent of any attachment of said vein support to tissue other than the vein.

\* \* \* \* \*